(12) United States Patent
Pericak-Vance et al.

(10) Patent No.: US 8,088,587 B2
(45) Date of Patent: Jan. 3, 2012

(54) GENETIC VARIANTS INCREASE THE RISK OF AGE-RELATED MACULAR DEGENERATION

(75) Inventors: Margaret A. Pericak-Vance, Durham, NC (US); Jonathan L. Haines, Nashville, TN (US); Eric Postel, Durham, NC (US); Anita Agarwal, Nashville, TN (US); Michael A. Hauser, Durham, NC (US); Silke Schmidt, Durham, NC (US); William K. Scott, Durham, NC (US)

(73) Assignees: Vanderbilt University, Nashville, TN (US); Duke University, Durham, NC (US)

( * ) Notice: Subject to any disclaimer, the term of this patent is extended or adjusted under 35 U.S.C. 154(b) by 745 days.

(21) Appl. No.: 11/885,336

(22) PCT Filed: Mar. 6, 2006

(86) PCT No.: PCT/US2006/007725
§ 371 (c)(1),
(2), (4) Date: Jul. 18, 2008

(87) PCT Pub. No.: WO2006/096561
PCT Pub. Date: Sep. 14, 2006

(65) Prior Publication Data
US 2010/0190264 A1 Jul. 29, 2010

Related U.S. Application Data

(60) Provisional application No. 60/658,208, filed on Mar. 4, 2005.

(51) Int. Cl.
*G01N 31/00* (2006.01)
*G01N 33/53* (2006.01)
(52) U.S. Cl. .......... 435/7.1; 435/4; 435/287.9; 436/501; 436/518; 436/525; 436/529; 436/535; 436/809; 530/300; 530/350; 422/50
(58) Field of Classification Search .................. 422/50
See application file for complete search history.

(56) References Cited

FOREIGN PATENT DOCUMENTS

| WO | 01-12823 A2 | 2/2001 |
|---|---|---|
| WO | 01-16364 A2 | 3/2001 |
| WO | 01-16364 A3 | 3/2001 |
| WO | WO 2006/088950 | 8/2006 |
| WO | WO 2006/096737 | 9/2006 |
| WO | WO 2006-133295 | 12/2006 |
| WO | WO 2007/022590 | 3/2007 |
| WO | WO 2007-029008 | 3/2007 |
| WO | WO 2007/044897 | 4/2007 |
| WO | WO 2007/056111 | 5/2007 |
| WO | WO 2007/056227 | 5/2007 |

OTHER PUBLICATIONS

Genbank Locus Y00716, "Human mRNA for Complement Factor H," Mar. 28, 1991, www.ncbi.nlm.nih.gov, pp. 1-3.
R. A. Hegele et al., "SNP Judgments and Freedom of Association," Arterioscler Thromb Vasc Biol. Jul. 1, 2002;22(7):1058-61.
U.T. Hacker et al., "Lack of Association Between an Interlukin-1 Receptor Antagonist Gene Polymorphism and Ulcerative Colitis," Gut. May 1997;40(5):623-7.
H. Jarva et al., "Regulation of Complement Activation by C-Reactive Protein: Targeting the Complement Inhibitory Activity of Factor H by an Interaction with Short Consensus Repeat Domains 7 and 8-11," J. Immunol. Oct. 1, 1999;163(7):3957-62.
M.K. Pnagburn et al., "Location of the Heparin-Binding Site on Compliment Factor," H. J. Biol. Chem., Sep. 5, 1991;266(25):16847-53.
Extended European Search Report dated Dec. 18, 2009 in Application No. 06736964-5.
Schultz, et al. "Analysis of the ARMD1 Locus: Evidence that a Mutation in HEMICENTIN-1 is Associated with Age-Related Macular Degeneration in a Large Family," Human Molecular Genetics, Oxford University Press, Surrey, vol. 12, No. 124, Dec. 15, 2003, pp. 0964-09606.
J. Haines et al., "Complement Factor H Variant Increases the Risk of Age-Related Macular Degeneration," Science, Apr. 15, 2005, vol. 308, pp. 419-421.
Rivera et al., "Hypothetical LOC387715 is a second major susceptibility gene for age-related macular degeneration, contributing independently of complement factor H to disease risk," Hum. Mol. Genet., 2005, 14: 3237-3236.

*Primary Examiner* — Lisa Cook
(74) *Attorney, Agent, or Firm* — Banner & Witcoff, Ltd.

(57) ABSTRACT

Age-related macular degeneration (AMD) is a leading cause of visual impairment and blindness in the elderly whose etiology remains largely unknown. Previous studies identified chromosome 1q32 as harboring a susceptibility locus for AMD, but it was not identified. We identified a strongly associated haplotype in two independent data sets. DNA sequencing of the complement factor II gene (CFII) within this haplotype revealed a coding variant, Y402II, that significantly increases the risk for AMD with odds ratios between 2.45 and 5.57. This identifies Complement factor II as involved in pathogenesis of AMD. This single variant alone is so common that it likely explains 43 percent of AMD in older adults. In addition, we have replicated and refined previous reports implicating a coding change in LOC387715 as the second major AMD susceptibility allele. The effect of rs10490924 appears to be completely independent of the Y402H variant in the CFH gene. The joint effect of these two susceptibility genes is consistent with a multiplicative model, and together, they may explain as much as 65% of the PAR of AMD. In contrast, the effect of rs10490924 appears to be strongly modified by cigarette smoking. Smoking and LOC387715 together may explain as much as 34% of AMD. Our data indicate that variant genotypes at rs10490924 confer a substantially larger AMD risk to cigarette smokers than non-smokers. This observation is supported by traditional case-control modeling, by ordered subset linkage analysis (OSA) incorporating pack-years of cigarette smoking as a covariate, and by family-based association analysis using a more homogeneous set of families as defined by OSA.

19 Claims, 20 Drawing Sheets

| | FAMILY DATASET | INDEPENDENT CASE CONTROL DATASET CASES | INDEPENDENT CASE CONTROL DATASET CONTROLS |
|---|---|---|---|
| NO. MULTIPLEX FAMILIES | 140 | -- | -- |
| NO. AFFECTED SIBLING PAIRS | 169 | -- | -- |
| NO. OTHER AFFECTED RELATIVE PAIRS | 37 | -- | -- |
| NO. SINGLETON FAMILIES | 60 | -- | -- |
| NO. DISCORDANT SIBLING PAIRS (MULTIPLEX AND SINGLETON FAMILIES) | 158 | -- | -- |
| NO. INDIVIDUALS | 526 | 610 | 259 |
| NO. GRADE 1 (%). NO DRUSEN OR SMALL (<63 µM) NONEXTENSIVE DRUSEN WITHOUT RPE ABNORMALITIES. | 85 (16.2%) | -- | 193 (22.2%) |
| NO. GRADE 2 (%). EXTENSIVE SMALL DRUSEN OR NONEXTENSIVE INTERMEDIATE DRUSEN (>=63 µM, < 125 µM) AND/OR RPE HYPER- OR HYPOPIGMENTATION. | 50 (9.5%) | -- | 66 (7.6%) |
| NO. GRADE 3 (%). EXTENSIVE INTERMEDIATE DRUSEN OR ANY LARGE, SOFT DRUSEN (>= 125µM), INCLUDING DRUSENOID RPE DETACHMENT. | 109 (20.7%) | 140 (16.1%) | -- |
| NO. GRADE 4 (%). GEOGRAPHIC ATROPHY (AREA OF RPE ATROPHY WITH SHARP MARGINS, USUALLY VISIBLE CHOROIDAL VESSELS, AT LEAST 175 µM DIAMETER). | 61 (11.6%) | 77 (8.9%) | -- |
| NO. GRADE 5 (%). EXUDATIVE AMD, INCLUDING NONDRUSENOID RPE DETACHMENT, CHOROIDAL NEOVASCULARIZATION, SUBRETINAL HEMORRHAGE OR FIBROSIS, OR PHOTOCOAGULATION SCAR CONSISTENT WITH TREATMENT OF AMD. | 221 (42.0%) | 393 (45.2%) | -- |
| MEAN AGE AT EXAMINATION (SD) | 72.6 (9.9) | 76.8 (7.7) | 66.7 (8.1) |
| % FEMALE | 66.2 | 64.9 | 57.1 |

FIG. 7

| SNP (RISK ALLELE) | GENE | TYPE | MAF$_{case}$ | MAF$_{control}$ | OR$_{het}$ (95%CI) | OR$_{hom}$ (95%CI) | p-value | GIST p-value |
|---|---|---|---|---|---|---|---|---|
| rs10490923 (G) | LOC387715 | His3Arg | 0.089 | 0.146 | 0.56 (0.36,0.86) | 0.19 (0.02,2.13) | 0.0037 | 0.77 |
| rs10490924 (T) | LOC387715 | Ala69Ser | 0.410 | 0.259 | 1.65 (1.12,2.43) | 5.73 (3.07,10.71) | 3.13E-08 | 0.05 |
| rs17623531 (G) | LOC387715 | Intronic | 0.087 | 0.146 | 0.55 (0.35,0.86) | 0.20 (0.02,2.19) | 0.0035 | 0.77 |
| A124205188G (G) | LOC387715 | Intronic | 0.412 | 0.257 | 1.70 (1.14,2.53) | 6.04 (3.22,11.33) | 1.34E-08 | 0.05 |
| rs3750848 (G) | LOC387715 | Intronic | 0.412 | 0.257 | 1.66 (1.12,2.47) | 5.93 (3.16,11.14) | 2.38E-08 | 0.05 |
| rs3750846 (G) | LOC387715 | Intronic | 0.409 | 0.264 | 1.52 (1.02,2.24) | 5.54 (2.96,10.38) | 1.44E-07 | 0.05 |
| rs10664316 (G) | LOC387715 | Intronic | 0.307 | 0.368 | 0.57 (0.38,0.83) | 0.55 (0.30,1.00) | 0.005 | 0.84 |
| rs11248321 (A) | CUZD1 | Intronic | 0.558 | 0.490 | 1.40 (0.89,2.22) | 2.37 (1.42,3.96) | 0.0009 | 0.41 |
| rs2950366 (A) | CUZD1 | Intronic | 0.435 | 0.487 | 0.56 (0.38,0.91) | 0.45 (0.26,0.77) | 0.0025 | 0.68 |
| rs1891110 (G) | CUZD1/ FAM24B | Leu2Pro (FAM24B); 5UTR (CUZD1) | 0.568 | 0.489 | 1.55 (0.90,2.68) | 3.24 (1.73,6.08) | 0.0002 | 0.51 |
| rs10902838 (A) | CUZD1 | Syn (LOC399815) | 0.539 | 0.482 | 1.20 (0.76,1.87) | 2.21 (1.32,3.70) | 0.0023 | 0.41 |
| rs2421141 (T) | LOC399815 | Intergenic | 0.540 | 0.488 | 1.17 (0.75,1.83) | 2.03 (1.22,3.39) | 0.0058 | 0.35 |
| rs4403744 (G) | | Intergenic | 0.542 | 0.490 | 1.16 (0.74,1.82) | 2.11 (1.25,3.56) | 0.0039 | 0.31 |
| rs2293435 (G) | FAM24A | 5' UTR | 0.537 | 0.466 | 1.51 (0.94,2.41) | 2.65 (1.53,4.61) | 0.0005 | 0.26 |
| rs6599638 (A) | C10ORF88 | Intronic | 0.493 | 0.427 | 1.57 (1.01,2.46) | 2.14 (1.25,3.66) | 0.0046 | 0.75 |

FIG. 8

| | Y402H | | | | | | | | |
|---|---|---|---|---|---|---|---|---|---|
| | Controls (n=208) | | | Cases (n=646) | | | OR (95% CI) | | |
| | TT | TC | CC | TT | TC | CC | TT | TC | CC |
| rs10490924 | | | | | | | | | |
| GG | 39 (18.8) | 57 (27.4) | 21 (10.1) | 35 (5.4) | 119 (18.4) | 69 (10.7) | 1.0 (REF) | 1.94 (0.98, 3.83) | 4.03 (1.80, 9.01) |
| GT | 21 (10.1) | 43 (20.7) | 10 (4.8) | 53 (8.2) | 124 (19.2) | 107 (16.6) | 2.72 (1.21, 6.12) | 2.66 (1.33, 5.33) | 12.59 (5.09, 31.15) |
| TT | 2 (1.0) | 12 (5.8) | 3 (1.4) | 35 (8.3) | 67 (10.4) | 48 (7.4) | 13.07 (2.4, 70.2) | 9.6 (3.9, 24.0) | 23.8 (6.3, 90.0) |

| P-value | | |
|---|---|---|
| TT | TC | CC |
| | 0.0579 | 0.0007 |
| 0.0156 | 0.0057 | <0.0001 |
| 0.0027 | <0.0001 | <0.0001 |

FIG. 9

| FACTOR 2 AND MODEL | AIC | AIC DIFFERENCE |
|---|---|---|
| Y402H (rs1061170) | | |
| MEAN | 936.8 | 262.4 |
| ADD1 | 852.0 | 177.6 |
| ADD2 | 719.2 | 44.8 |
| ADDBOTH | 675.3 | 0.9 |
| DOM1 | 851.5 | 177.1 |
| DOM2 | 719.1 | 44.7 |
| DOMBOTH | 674.4 | 0 (BEST FIT) |
| ADDINT | 677.2 | 2.8 |
| ADDDOM | 677.5 | 3.1 |
| DOMINT | 678.5 | 4.1 |
| SMOKING (EVER VS. NEVER) | | |
| MEAN | 936.8 | 288.0 |
| ADD | 852.0 | 203.2 |
| SMOKE | 708.5 | 59.7 |
| ADD_SMOKE | 654.0 | 5.2 |
| DOM | 851.5 | 202.7 |
| ADD_SMOKE_INT | 648.8 | 0 (BEST FIT) |
| DOM_SMOKE_INT | 652.4 | 3.6 |

FIG. 10

SMOKING HISTORY

| | Controls (n=211) | | Cases (n=521) | | OR (95% CI) | | p-value | |
|---|---|---|---|---|---|---|---|---|
| | NEVER | EVER | NEVER | EVER | NEVER | EVER | NEVER | EVER |
| rs10490924 | | | | | | | | |
| GG | 57 (27.0) | 62 (29.4) | 84 (16.1) | 103 (19.8) | 1.0 (REF) | 0.93 (0.53,1.64) | — | 0.80 |
| GT | 39 (18.5) | 34 (16.1) | 87 (16.7) | 135 (25.9) | 1.19 (0.63,2.22) | 2.69 (1.47,4.92) | 0.59 | 0.001 |
| TT | 10 (4.7) | 9 (4.3) | 36 (6.9) | 76 (14.6) | 2.07 (0.83,5.14) | 8.15 (3.46,19.18) | 0.12 | <0.0001 |

FIG. 11

| AMD GRADE | SMOKERS | | | | NON-SMOKERS | | | | ALL GENOTYPED INDIVIDUALS | | | |
|---|---|---|---|---|---|---|---|---|---|---|---|---|
| | MAF | GENOTYPE GG | GT | TT | MAF | GENOTYPE GG | GT | TT | MAF | GENOTYPE GG | GT | TT |
| 1 | .243 | .597 (43) | .319 (23) | .083 (6) | .247 | .582 (43) | .342 (27) | .076 (6) | .275 | .520 (140) | .409 (110) | .071 (19) |
| 2 | .258 | .576 (19) | .333 (11) | .091 (3) | .370 | .407 (11) | .444 (12) | .148 (4) | .307 | .479 (57) | .429 (51) | .092 (11) |
| 3 | .326 | .478 (33) | .391 (27) | .130 (9) | .308 | .467 (28) | .450 (27) | .083 (5) | .318 | .460 (115) | .444 (111) | .096 (24) |
| 4 | .378 | .405 (15) | .432 (16) | .162 (6) | .289 | .615 (16) | .192 (5) | .192 (5) | .390 | .404 (55) | .412 (56) | .184 (25) |
| 5 | .514 | .264 (55) | .442 (92) | .293 (61) | .442 | .331 (40) | .454 (55) | .215 (26) | .476 | .295 (177) | .458 (275) | .247 (148) |

FIG. 12

| | MINOR ALLELE FREQUENCY | | | |
|---|---|---|---|---|
| | INDIVIDUALS HOMOZYGOUS FOR rs1891110 VARIANT | | INDIVIDUALS HOMOZYGOUS FOR rs10490924 VARIANT | |
| VARIANT | GRADE 1 | GRADE 5 | GRADE 1 | GRADE 5 |
| rs10490923 | A=0.11 | A=0.14 | ND | ND |
| rs2736911 | T=0.188 | T=0.159 | ND | ND |
| rs10490924 | T=0.188 | T=0.523 | ND | ND |
| rs17623531 | T=0.11 | T=0.077 | ND | ND |
| C124204957T | T=1 | T=0.4 | ND | ND |
| G124204966T | T=0.060 | T=0.538 | T=1 | T=1 |
| A124205188G | G=0.189 | G=0.523 | G=0.974 | G=0.983 |
| T124205201C | C=0.189 | C=0.523 | C=0.974 | C=0.983 |
| rs3750848 | G=0.189 | G=0.523 | G=0.974 | G=0.983 |
| rs3750846 | C=0.189 | C=0.523 | C=1 | C=1 |
| rs2736912 | T=0.167 | T=0.182 | ND | ND |
| rs3750847 | T=0.189 | T=0.523 | T=1 | T=1 |
| rs10664316 | AT=0.66 | AT=0.94 | AT=1 | AT=1 |
| T124206387C | C=0.15 | C=0.16 | ND | ND |
| rs7088128 | G=0.15 | G=0.16 | ND | ND |

FIG. 13

| | MINOR ALLELE FREQUENCY | | |
|---|---|---|---|
| VARIANT | GRADE 1 | GRADE 3 | GRADE 5 |
| rs7908196 | A=0.184 | ND | A=0.095 |
| rs11248321 | A=0.065 | A=0.023 | A=0.044 |
| A124585820G | G=0.022 | G=0 | G=0 |
| C124586887T | T=0 | T=0 | T=0.021 |
| A124586911G | G=0.022 | T=0 | G=0 |
| C124587151T | T=0 | T=0 | T=0.021 |
| A124590492G | G=0 | G=0 | G=0.024 |
| C124595656T | T=0.136 | T=0 | T=0.136 |
| C124599157T | T=0 | T=0 | T=0.022 |
| C124599185T | T=0 | T=0 | T=0.022 |
| A124601941T | T=0 | T=0 | T=0.022 |
| G124608497A | A=0 | A=0 | A=0.021 |
| A124612240G | G=0 | G=0 | G=0.021 |
| A124612340G | G=0.043 | G=0.063 | G=0.042 |
| G124612380A | A=0 | A=0 | A=0.021 |
| T124612649C | C=0 | C=0 | C=0.021 |
| rs4638251 | A=0.184 | A=0.341 | A=0.357 |
| T124628837C | C=0 | C=0.045 | C=0.024 |
| C124629013T | T=0 | T=0 | T=0.024 |
| A124629083G | G=0 | G=0 | G=0.024 |
| rs2950355 | T=0.09 | T=0.022 | T=0.087 |
| rs2950354 | T=0.048 | T=0 | T=0 |
| rs9423288 | T=0.048 | T=0 | T=0 |
| rs10902838 | A=0.095 | A=0 | A=0 |
| rs11248323 | T=0.048 | T=0 | T=0 |
| T124647361A | A=0 | A=0 | A=0.022 |
| rs11248329 | C=0.043 | C=0.022 | C=0.043 |
| rs4403744 | G=0.087 | G=0.022 | G=0.114 |
| rs1891113 | T=0.0 | T=0.023 | T=0 |

FIG. 14

| SNP | Position(Mb) | MAF$_{case}$ | MAF$_{control}$ | P-Value |
|---|---|---|---|---|
| rs11194997 | 111.879769 | 15.17 | 14.15 | 0.3657 |
| rs1800544 | 112.826493 | 28.50 | 27.68 | 0.5875 |
| rs958249 | 113.554620 | 44.42 | 43.35 | 0.2503 |
| rs10787428 | 113.925369 | 40.76 | 40.99 | 0.7399 |
| rs7904701 | 114.036798 | 32.80 | 35.11 | 0.6628 |
| rs10749118 | 114.139469 | 49.63 | 46.63 | 0.4949 |
| rs2290966 | 114.232744 | 30.61 | 32.12 | 0.5268 |
| rs1325172 | 114.348545 | 21.25 | 20.06 | 0.4370 |
| rs7088368 | 114.448919 | 28.76 | 26.00 | 0.3213 |
| rs10787464 | 114.542952 | 44.01 | 41.81 | 0.7456 |
| rs1556014 | 114.644187 | 30.93 | 30.62 | 0.3892 |
| rs4074720 | 114.738487 | 45.49 | 44.92 | 0.6558 |
| rs11196218 | 114.830484 | 25.67 | 27.33 | 0.8677 |
| rs7906315 | 114.877208 | 37.22 | 37.80 | 0.9055 |
| rs2616637 | 115.958421 | 38.41 | 42.98 | 0.0960 |
| rs6585309 | 116.720327 | 41.19 | 40.94 | 0.8082 |
| rs2769371 | 117.331117 | 49.49 | 49.08 | 0.8196 |
| rs2804147 | 117.429024 | 28.61 | 26.67 | 0.3666 |
| rs2907582 | 117.539017 | 26.61 | 23.85 | 0.5258 |
| rs1017822 | 117.631567 | 41.55 | 37.05 | 0.1099 |
| rs180557 | 117.804876 | 17.70 | 15.88 | 0.7130 |
| rs2245020 | 117.874940 | 41.73 | 45.17 | 0.0708 |
| rs12762746 | 117.929358 | 39.60 | 36.47 | 0.4447 |
| rs7096877 | 117.981630 | 31.28 | 34.39 | 0.2973 |
| rs730357 | 118.008541 | 26.15 | 24.32 | 0.7555 |
| rs7906587 | 118.221656 | 6.37 | 8.26 | 0.1816 |
| rs1867991 | 118.341895 | 28.53 | 31.25 | 0.5100 |
| rs3010460 | 118.432901 | 32.70 | 35.45 | 0.4359 |
| rs2291316 | 118.584279 | 51.61 | 50.00 | 0.6276 |
| rs1419832 | 118.660272 | 25.56 | 26.04 | 0.9785 |
| rs1905539 | 118.729304 | 24.15 | 23.73 | 0.9160 |
| rs363390 | 118.994069 | 23.95 | 20.55 | 0.2086 |
| rs2240776 | 119.297514 | 39.46 | 36.01 | 0.3524 |
| rs71003 | 119.339751 | 44.46 | 41.71 | 0.1828 |
| rs1343418 | 119.625940 | 47.08 | 49.08 | 0.5243 |
| rs853600 | 119.889137 | 43.28 | 38.53 | 0.1423 |
| rs722525 | 120.089604 | 20.19 | 21.22 | 0.9018 |
| rs1857269 | 120.162626 | 39.68 | 37.01 | 0.3345 |
| rs2292767 | 120.340026 | 38.78 | 39.20 | 0.5080 |
| rs4752182 | 120.387121 | 41.61 | 43.75 | 0.5518 |

FIG. 15A

| | | | | |
|---|---|---|---|---|
| rs17586536 | 120.470153 | 34.15 | 35.20 | 0.7424 |
| rs754059 | 120.560500 | 40.72 | 38.66 | 0.4950 |
| rs10787879 | 120.677560 | 21.34 | 20.74 | 0.9425 |
| rs7905458 | 120.775544 | 42.11 | 43.82 | 0.7598 |
| rs3740558 | 120.909169 | 53.32 | 46.76 | 0.2271 |
| rs11198856 | 121.031688 | 27.41 | 30.40 | 0.4797 |
| rs871196 | 121.059064 | 32.20 | 29.77 | 0.5918 |
| rs1537576 | 121.167523 | 48.63 | 46.33 | 0.0664 |
| rs1467813 | 121.271597 | 27.91 | 29.33 | 0.7669 |
| rs3781503 | 121.561497 | 42.75 | 47.43 | 0.0440 |
| rs2475298 | 121.669003 | 33.82 | 35.23 | 0.3181 |
| rs11597362 | 121.740877 | 9.43 | 9.89 | 0.8438 |
| rs7907490 | 121.912689 | 29.63 | 33.33 | 0.1894 |
| rs914483 | 121.958557 | 46.50 | 46.61 | 0.3342 |
| rs2901228 | 121.105373 | 26.35 | 26.40 | 0.9874 |
| rs7916482 | 122.164552 | 21.99 | 18.75 | 0.5720 |
| rs1571101 | 122.260407 | 52.92 | 48.55 | 0.4508 |
| rs11199431 | 122.345000 | 35.07 | 41.01 | 0.0793 |
| rs2901256 | 122.373794 | 41.00 | 41.98 | 0.9378 |
| rs7475474 | 122.419759 | 41.34 | 44.85 | 0.2049 |
| rs3011415 | 122.498315 | 16.30 | 15.81 | 0.8845 |
| rs7092824 | 122.553883 | 23.09 | 20.41 | 0.4129 |
| rs2241846 | 122.608138 | 19.46 | 19.14 | 0.9659 |
| rs4751808 | 122.667052 | 40.46 | 43.72 | 0.3188 |
| rs934321 | 122.704274 | 23.51 | 22.29 | 0.9843 |
| rs6585684 | 122.756837 | 44.14 | 46.01 | 0.6289 |
| rs2420900 | 122.818664 | 35.14 | 37.07 | 0.2867 |
| rs12771493 | 122.871377 | 16.95 | 17.06 | 0.3750 |
| rs7085142 | 122.929364 | 36.27 | 36.61 | 0.8429 |
| rs10749409 | 122.966556 | 30.10 | 31.28 | 0.9783 |
| rs3925042 | 123.009010 | 35.67 | 35.98 | 0.8212 |
| rs4752528 | 123.049774 | 46.13 | 41.12 | 0.1969 |
| rs7895870 | 123.088239 | 42.77 | 40.85 | 0.1074 |
| rs2420936 | 123.198871 | 49.21 | 45.96 | 0.3439 |
| rs6585740 | 123.218199 | 23.11 | 25.23 | 0.7064 |
| rs3135831 | 123.226910 | 43.95 | 47.44 | 0.1856 |
| rs2981461 | 123.237027 | 42.29 | 34.86 | 0.0809 |
| rs2061616 | 123.269785 | 31.66 | 34.72 | 0.6967 |
| rs2981430 | 123.301688 | 43.42 | 42.14 | 0.4744 |
| rs1863744 | 123.348263 | 12.07 | 12.71 | 0.6090 |
| rs7902581 | 123.395470 | 26.79 | 25.92 | 0.2902 |
| rs7900009 | 123.450068 | 43.35 | 46.51 | 0.5352 |
| rs2935706 | 123.481658 | 22.20 | 22.83 | 0.8291 |
| rs12718345 | 123.562182 | 44.93 | 45.98 | 0.9321 |
| rs10887005 | 123.621430 | 34.92 | 32.21 | 0.3005 |

FIG. 15B

| | | | | |
|---|---|---|---|---|
| rs11200251 | 123.663196 | 31.78 | 24.85 | 0.0378 |
| rs3750839 | 123.762897 | 20.02 | 18.34 | 0.5261 |
| rs10887058 | 123.803749 | 34.00 | 31.25 | 0.0646 |
| rs2420992 | 123.847423 | 43.50 | 40.68 | 0.1798 |
| rs7920046 | 123.936833 | 45.61 | 49.72 | 0.2042 |
| rs2295879 | 123.986966 | 28.54 | 33.80 | 0.2575 |
| rs6585810 | 124.031437 | 44.61 | 42.48 | 0.4722 |
| rs927427 | 124.078715 | 48.17 | 44.53 | 0.3191 |
| rs2421013 | 124.079026 | 47.88 | 44.41 | 0.6140 |
| rs1048347 | 124.086051 | 35.64 | 35.51 | 0.7427 |
| rs4146894 | 124.145371 | 39.07 | 47.58 | 0.0281 |
| rs4405249 | 124.173722 | 11.54 | 13.27 | 0.4390 |
| rs2292625 | 124.176357 | 13.01 | 14.92 | 0.5921 |
| rs1045216 | 124.179187 | 28.22 | 36.80 | 0.0215 |
| rs1882907 | 124.198389 | 12.59 | 14.17 | 0.3805 |
| rs10490923 | 124.204241 | 8.91 | 14.63 | 0.0037 |
| rs2736911 | 124.204345 | 12.54 | 13.36 | 0.5683 |
| rs10490924 | 124.204438 | 40.97 | 25.90 | 3.13E-08 |
| rs17623531 | 124.204911 | 8.66 | 14.57 | 0.0035 |
| A124,205,188G | 124.205188 | 41.20 | 25.71 | 1.34E-08 |
| rs3750848 | 124.205305 | 41.20 | 25.71 | 2.38E-08 |
| rs7750846 | 124.205555 | 40.87 | 26.41 | 1.44E-07 |
| rs2736912 | 124.205584 | 12.84 | 12.92 | 0.8743 |
| rs10664316 | 124.206376 | 30.72 | 36.84 | 0.0052 |
| rs4752700 | 124.227602 | 40.75 | 45.45 | 0.0753 |
| rs760336 | 124.228700 | 41.43 | 45.47 | 0.1434 |
| rs763720 | 124.252434 | 27.97 | 24.04 | 0.1487 |
| rs1052715 | 124.392667 | 39.24 | 34.62 | 0.1861 |
| rs7913531 | 124.446023 | 36.46 | 42.33 | 0.0102 |
| rs2421125 | 124.485953 | 29.31 | 29.17 | 0.7618 |
| rs947260 | 124.518920 | 46.81 | 44.38 | 0.1978 |
| rs10902963 | 124.534564 | 1.92 | 2.34 | 0.9541 |
| rs7895725 | 124.565363 | 21.74 | 21.77 | 0.4276 |
| rs11248317 | 124.575823 | 20.66 | 20.47 | 0.3999 |
| rs11248321 | 124.584143 | 55.82 | 48.96 | 0.0009 |
| rs2950366 | 124.591504 | 43.46 | 48.71 | 0.0025 |
| rs1891110 | 124.600017 | 56.83 | 48.86 | 0.0002 |
| A124,612,340G | 124.612340 | 5.09 | 4.20 | 0.1559 |
| rs4638251 | 124.628817 | 19.14 | 17.80 | 0.6975 |
| T124,628,837C | 124.628837 | 2.95 | 3.17 | 0.7469 |
| rs2950355 | 124.637423 | 2.26 | 2.02 | 0.7642 |
| rs2950354 | 124.637881 | 1.75 | 1.91 | 0.9718 |
| rs9423288 | 124.637962 | 2.34 | 2.19 | 0.7982 |
| rs10902838 | 124.638140 | 53.88 | 48.19 | 0.0023 |
| rs2421141 | 124.640426 | 54.04 | 48.78 | 0.0058 |

FIG. 15C

| | | | | |
|---|---|---|---|---|
| rs11248329 | 124.647547 | 2.25 | 24.85 | 0.6796 |
| rs4403744 | 124.647988 | 54.25 | 18.34 | 0.0039 |
| rs12354676 | 124.651710 | 1.43 | 31.25 | 0.8196 |
| rs2293435 | 124.660259 | 53.06 | 40.68 | 0.0005 |
| rs6599638 | 124.694139 | 49.29 | 49.72 | 0.0046 |
| rs9328842 | 124.755847 | 31.23 | 33.80 | 0.4346 |
| rs7070793 | 124.779176 | 40.62 | 42.48 | 0.4845 |
| rs4980248 | 124.817155 | 38.45 | 44.53 | 0.6714 |
| rs2495774 | 124.922076 | 49.19 | 44.41 | 0.8188 |
| rs7917062 | 125.029766 | 11.46 | 35.51 | 0.2795 |
| rs7894765 | 125.115141 | 33.89 | 47.58 | 0.5345 |
| rs7916586 | 125.152183 | 39.71 | 13.27 | 0.5677 |
| rs11248532 | 125.195394 | 24.46 | 14.92 | 0.4149 |
| rs1556852 | 125.238440 | 45.28 | 36.80 | 0.7321 |
| rs1123012 | 125.410980 | 43.52 | 14.17 | 0.4423 |
| rs4980202 | 125.453594 | 32.39 | 14.63 | 0.9465 |
| rs9060 | 125.495443 | 30.22 | 13.36 | 0.7472 |
| rs1914525 | 125.535626 | 15.72 | 25.90 | 0.2056 |
| rs7071385 | 125.592528 | 22.51 | 14.57 | 0.1366 |
| rs7090117 | 125.639455 | 13.32 | 25.71 | 0.9231 |
| rs6588744 | 125.703882 | 46.94 | 25.71 | 0.7689 |
| rs4929810 | 125.740110 | 23.73 | 26.41 | 0.5292 |
| rs4397783 | 125.839415 | 32.24 | 12.92 | 0.4952 |
| rs7078615 | 125.853202 | 27.98 | 36.84 | 0.1094 |
| rs7905355 | 125.914585 | 35.93 | 45.45 | 0.8753 |
| rs4962394 | 125.951488 | 32.11 | 45.47 | 0.4991 |
| rs4962728 | 125.998970 | 44.83 | 24.04 | 0.6571 |
| rs7068170 | 126.067579 | 32.93 | 34.62 | 0.0615 |
| rs11597880 | 126.068262 | 34.77 | 42.33 | 0.0083 |
| rs908366 | 126.134829 | 35.40 | 29.17 | 0.6351 |
| rs3824809 | 126.175697 | 28.26 | 44.38 | 0.4645 |
| rs2045184 | 126.205294 | 38.06 | 2.34 | 0.2144 |
| rs12769430 | 126.231378 | 53.72 | 21.77 | 0.1656 |
| rs7923479 | 126.285545 | 34.70 | 20.47 | 0.8067 |
| rs10736889 | 126.328647 | 38.27 | 48.96 | 0.4949 |
| rs4962683 | 126.361947 | 30.40 | 48.71 | 0.5699 |
| rs10794178 | 126.401914 | 34.93 | 48.86 | 0.1605 |
| rs2280450 | 126.426269 | 46.97 | 4.20 | 0.0644 |
| rs2303611 | 126.507979 | 45.66 | 17.80 | 0.0884 |
| rs7923382 | 126.566493 | 25.41 | 3.17 | 0.5993 |
| rs10901841 | 126.622376 | 24.10 | 2.02 | 0.8163 |
| rs718949 | 126.729019 | 23.31 | 1.91 | 0.4998 |
| rs1715873 | 126.815593 | 18.81 | 2.19 | 0.4636 |
| rs2886276 | 126.904176 | 37.92 | 48.19 | 0.7160 |
| rs2017040 | 127.071823 | 31.65 | 48.78 | 0.9394 |

FIG. 15D

| rs768761 | 127.124751 | 30.02 | 26.92 | 0.2250 |
|---|---|---|---|---|
| rs2304264 | 127.254905 | 8.50 | 8.76 | 0.8927 |
| rs9422913 | 127.335597 | 11.47 | 10.60 | 0.8795 |
| rs7922546 | 127.450743 | 36.03 | 34.46 | 0.6909 |
| rs2281955 | 127.474607 | 43.30 | 47.24 | 0.2344 |
| rs7095359 | 127.951592 | 20.66 | 21.18 | 0.5940 |
| rs2766070 | 128.978367 | 47.17 | 44.51 | 0.3078 |
| rs1001990 | 130.298844 | 28.52 | 23.84 | 0.0510 |
| rs7091540 | 131.310266 | 50.25 | 44.82 | 0.0963 |
| rs913628 | 131.945479 | 25.43 | 23.81 | 0.6598 |

FIG. 15E

SEQUENCE LISTING

```
<160> NUMBER OF SEQ ID NOS: 56

<210> SEQ ID NO 1
<211> LENGTH: 3926
<212> TYPE: DNA
<213> ORGANISM: Homo sapiens
<220> FEATURE:
<221> NAME/KEY: CDS
<222> LOCATION: (74)...(3767)
<220> FEATURE:
<221> NAME/KEY: variation
<222> LOCATION: (1277)...(1277)
<223> OTHER INFORMATION: polymorphic variation

<400> SEQUENCE: 1
aattcttgga agaggagaac tggacgttgt gaacagagtt agctggtaaa tgtcctctta      60
aaagatccaa aaaatgagac ttctagcaaa gattatttgc cttatgttat gggctatttg     120
```

```
tgtagcagaa gattgcaatg aacttcctcc aagaagaaat acagaaattc tgacaggttc      180
ctggtctgac caaacatatc cagaaggcac ccaggctatc tataaatgcc gccctggata      240
tagatctctt ggaaatgtaa taatggtatg caggaaggga gaatgggttg ctcttaatcc      300
attaaggaaa tgtcagaaaa ggccctgtgg acatcctgga gatactcctt ttggtacttt      360 taccccttaca ggaggaaatg tgtttgaata tggtgtaaaa gctgtgtata catgtaatga      420
ggggtatcaa ttgctaggtg agattaatta ccgtgaatgt gacacagatg gatggaccaa      480
tgatattcct atatgtgaag ttgtgaagtg tttaccagtg acagcaccag agaatggaaa      540
aattgtcagt agtgcaatgg aaccagatcg ggaataccat tttggacaag cagtacggtt      600
tgtatgtaac tcaggctaca agattgaagg agatgaagaa atgcattgtt cagacgatgg      660
tttttggagt aaagagaaac caagtgtgt ggaaatttca tgcaaatccc cagatgttat      720
aaatggatct cctatatctc agaagattat ttataaggag aatgaacgat ttcaatataa      780
atgtaacatg ggttatgaat acagtgaaag aggagatgct gtatgcactg aatctggatg      840
gcgtccgttg ccttcatgtg aagaaaaatc atgtgataat ccttatattc caaatggtga      900
ctactcacct ttaaggatta aacacagaac tggagatgaa atcacgtacc agtgtagaaa      960 tggttttat cctgcaaccc ggggaaatac agccaaatgc acaagtactg gctggatacc     1020
tgctccgaga tgtaccttga aaccttgtga ttatccagac attaaacatg gaggtctata     1080
tcatgagaat atgcgtagac catactttcc agtagctgta ggaaaatatt actcctatta     1140
ctgtgatgaa cattttgaga ctccgtcagg aagttactgg gatcacattc attgcacaca     1200
agatggatgg tcgccagcag taccatgcct cagaaaatgt tattttcctt atttggaaaa     1260
tggatataat caaaattatg gaagaaagtt tgtacagggt aaatctatag acgttgcctg     1320
ccatcctggc tacgctcttc caaaagcgca gaccacagtt acatgtatgg agaatggctg     1380
gtctcctact cccagatgca tccgtgtcaa aacatgttcc aaatcaagta tagatattga     1440
gaatgggttt atttctgaat ctcagtatac atatgcctta aaagaaaaag cgaaatatca     1500 atgcaaaacta ggatatgtaa cagcagatgg tgaaacatca ggatcaatta gatgtgggaa     1560
agatggatgg tcagctcaac ccacgtgcat taaatcttgt gatatcccag tatttatgaa     1620
tgccagaact aaaaatgact tcacatggtt taagctgaat gacacattgg actatgaatg     1680
ccatgatggt tatgaaagca atactggaag caccactggt tccatagtgt gtggttacaa     1740
tggttggtct gatttaccca tatgttatga aagagaatgc gaacttccta aaatagatgt     1800
acacttagtt cctgatcgca agaaagacca gtataaagtt ggagaggtgt tgaaattctc     1860
ctgcaaacca ggatttacaa tagttggacc taattccgtt cagtgctacc actttggatt     1920
gtctcctgac ctcccaatat gtaaagagca agtacaatca tgtggtccac ctcctgaact     1980
cctcaatggg aatgttaagg aaaaaacgaa agaagaatat ggacacagtg aagtggtgga     2040
atattattgc aatcctagat ttctaatgaa gggacctaat aaaattcaat gtgttgatgg     2100
agagtggaca actttaccag tgtgtattgt ggaggagagt acctgtggag atatacctga     2160
acttgaacat ggctgggccc agcttttcttc ccctccttat tactatggag attcagtgga     2220
attcaattgc tcagaatcat ttacaatgat tggacacaga tcaattacgt gtattcatgg     2280
agtatggacc caacttcccc agtgtgtggc aatagataaa cttaagaagt gcaaatcatc     2340
aaatttaatt atacttgagg aacatttaaa aaacaagaag gaattcgatc ataattctaa     2400
cataaggtac agatgtagag gaaaagaagg atggatacac acagtctgca taaatggaag     2460
atgggatcca gaagtgaact gctcaatggc acaaatacaa ttatgcccac ctccacctca     2520
```

```
gattcccaat tctcacaata tgacaaccac actgaattat cgggatggag aaaaagtatc    2580
tgttctttgc caagaaaatt atctaattca ggaaggagaa gaaattacat gcaaagatgg    2640
aagatggcag tcaataccac tctgtgttga aaaaattcca tgttcacaac cacctcagat    2700
agaacacgga accattaatt catccaggtc ttcacaagaa agttatgcac atgggactaa    2760
attgagttat acttgtgagg gtggtttcag gatatctgaa gaaaatgaaa caacatgcta    2820
catgggaaaa tggagttctc cacctcagtg tgaaggcctt ccttgtaaat ctccacctga    2880
gatttctcat ggtgttgtag ctcacatgtc agacagttat cagtatggag aagaagttac    2940
gtacaaatgt tttgaaggtt ttggaattga tgggcctgca attgcaaaat gcttaggaga    3000
aaaatggtct caccctccat catgcataaa aacagattgt ctcagtttac ctagctttga    3060
aaatgccata cccatgggag agaagaagga tgtgtataag gcgggtgagc aagtgactta    3120
cacttgtgca acatattaca aaatggatgg agccagtaat gtaacatgca ttaatagcag    3180
atggacagga aggccaacat gcagagacac ctcctgtgtg aatccgccca cagtacaaaa    3240
tgcttatata gtgtcgagac agatgagtaa atatccatct ggtgagagag tacgttatca    3300
atgtaggagc cctatgaaa tgtttgggga tgaagaagtg atgtgtttaa atggaaactg    3360
gacggaacca cctcaatgca aagattctac aggaaaatgt gggcccctc cacctattga    3420 caatggggac attacttcat tcccgttgtc agtatatgct ccagcttcat cagttgagta    3480
ccaatgccag aacttgtatc aacttgaggg taacaagcga ataacatgta gaaatggaca    3540
atggtcagaa ccaccaaaat gcttacatcc gtgtgtaata tcccgagaaa ttatggaaaa    3600
ttataacata gcattaaggt ggacagccaa acagaagctt tattcgagaa caggtgaatc    3660
agttgaattt gtgtgtaaac ggggatatcg tctttcatca cgttctcaca cattgcgaac    3720
aacatgttgg gatgggaaac tggagtatcc aacttgtgca aaaagataga atcaatcata    3780
aagtgcacac ctttattcag aactttagta ttaaatcagt tctcaatttc attttttatg    3840
tattgtttta ctccttttta ttcatacgta aaattttgga ttaatttgtg aaaatgtaat    3900
tataagctga gaccggtggc tctctt                                         3926
```

```
<210> SEQ ID NO 2
<211> LENGTH: 3926
<212> TYPE: DNA
<213> ORGANISM: Homo sapiens
<220> FEATURE:
<221> NAME/KEY: CDS
<222> LOCATION: (74)...(3767)
<220> FEATURE:
<221> NAME/KEY: variation
<222> LOCATION: (1277)...(1277)
<223> OTHER INFORMATION: polymorphic variant

<400> SEQUENCE: 2
aattcttgga agaggagaac tggacgttgt gaacagagtt agctggtaaa tgtcctctta     60
aaagatccaa aaaatgagac ttctagcaaa gattatttgc cttatgttat gggctatttg    120
tgtagcagaa gattgcaatg aacttcctcc aagaagaaat acagaaattc tgacaggttc    180
ctggtctgac caaacatatc cagaaggcac ccaggctatc tataaatgcc gccctggata    240
tagatctctt ggaaatgtaa taatggtatg caggaaggga gaatgggttg ctcttaatcc    300
attaaggaaa tgtcagaaaa ggccctgtgg acatcctgga gatactcctt ttggtacttt    360 taccccttaca ggaggaaatg tgtttgaata tggtgtaaaa gctgtgtata catgtaatga    420
ggggtatcaa ttgctaggtg agattaatta ccgtgaatgt gacacagatg gatggaccaa    480
```

```
tgatattcct atatgtgaag ttgtgaagtg tttaccagtg acagcaccag agaatggaaa    540
aattgtcagt agtgcaatgg aaccagatcg ggaataccat tttggacaag cagtacggtt    600
tgtatgtaac tcaggctaca agattgaagg agatgaagaa atgcattgtt cagacgatgg    660
tttttggagt aaagagaaac caaagtgtgt ggaaatttca tgcaaatccc cagatgttat    720
aaatggatct cctatatctc agaagattat ttataaggag aatgaacgat ttcaatataa    780
atgtaacatg ggttatgaat acagtgaaag aggagatgct gtatgcactg aatctggatg    840
gcgtccgttg ccttcatgtg aagaaaaatc atgtgataat ccttatattc caaatggtga    900
ctactcacct ttaaggatta aacacagaac tggagatgaa atcacgtacc agtgtagaaa    960
tggtttttat cctgcaaccc ggggaaatac agccaaatgc acaagtactg gctggatacc   1020
tgctccgaga tgtaccttga aaccttgtga ttatccagac attaaacatg aggtctata    1080 tcatgagaat atgcgtagac atactttcc agtagctgta ggaaaatatt actcctatta    1140
ctgtgatgaa catttttgaga ctccgtcagg aagttactgg gatcacattc attgcacaca   1200
agatggatgg tcgccagcag taccatgcct cagaaaatgt tattttcctt atttggaaaa   1260
tggatataat caaaatcatg gaagaaagtt tgtacagggt aaatctatag acgttgcctg   1320
ccatcctggc tacgctcttc caaaagcgca gaccacagtt acatgtatgg agaatggctg   1380
gtctcctact cccagatgca tccgtgtcaa aacatgttcc aaatcaagta tagatattga   1440
gaatgggttt atttctgaat ctcagtatac atatgcctta aaagaaaaag cgaaatatca   1500
atgcaaacta ggatatgtaa cagcagatgg tgaaacatca ggatcaatta gatgtgggaa   1560
agatggatgg tcagctcaac ccacgtgcat taaatcttgt gatatcccag tatttatgaa   1620
tgccagaact aaaaatgact tcacatggtt taagctgaat gacacattgg actatgaatg   1680
ccatgatggt tatgaaagca atactggaag caccactggt tccatagtgt gtggttacaa   1740
tggttggtct gatttaccca tatgttatga aagagaatgc gaacttccta aaatagatgt   1800
acacttagtt cctgatcgca agaaagacca gtataaagtt ggagaggtgt tgaaattctc   1860
ctgcaaacca ggatttacaa tagttggacc taattccgtt cagtgctacc actttggatt   1920
gtctcctgac ctcccaatat gtaaagagca agtacaatca tgtggtccac tcctgaact   1980 cctcaatggg aatgttaagg aaaaaacgaa agaagaatat ggacacagtg aagtggtgga   2040
atattattgc aatcctagat ttctaatgaa gggacctaat aaaattcaat gtgttgatgg   2100
agagtggaca acttaccag tgtgtattgt ggaggagagt acctgtggag atatacctga   2160
acttgaacat ggctgggccc agcttttcttc ccctccttat tactatggag attcagtgga   2220
attcaattgc tcagaatcat ttacaatgat tggacacaga tcaattacgt gtattcatgg   2280 agtatgggacc caacttcccc agtgtgtggc aatagataaa cttaagaagt gcaaatcatc   2340
aaatttaatt atacttgagg aacatttaaa aaacaagaag gaattcgatc ataattctaa   2400
cataaggtac agatgtagag gaaaagaagg atggatacac acagtctgca taaatggaag   2460
atgggatcca gaagtgaact gctcaatggc acaaatacaa ttatgcccac ctccacctca   2520
gattcccaat tctcacaata tgacaaccac actgaattat cgggatggag aaaaagtatc   2580
tgttctttgc caagaaaatt atctaattca ggaaggagaa gaaattacat gcaaagatgg   2640
aagatggcag tcaataccac tctgtgttga aaaaattcca tgttcacaac cacctcagat   2700
agaacacgga accattaatt catccaggtc ttcacaagaa agttatgcac atgggactaa   2760
attgagttat acttgtgagg gtggtttcag gatatctgaa gaaaatgaaa caacatgcta   2820
catgggaaaa tggagttctc cacctcagtg tgaaggcctt ccttgtaaat ctccacctga   2880
```

-continued

```
gatttctcat ggtgttgtag ctcacatgtc agacagttat cagtatggag aagaagttac    2940
gtacaaatgt tttgaaggtt ttggaattga tgggcctgca attgcaaaat gcttaggaga    3000
aaaatggtct caccctccat catgcataaa aacagattgt ctcagtttac ctagctttga    3060
aaatgccata cccatgggag agaagaagga tgtgtataag gcgggtgagc aagtgactta    3120
cacttgtgca acatattaca aaatggatgg agccagtaat gtaacatgca ttaatagcag    3180
atggacagga aggccaacat gcagagacac ctcctgtgtg aatccgccca cagtacaaaa    3240
tgcttatata gtgtcgagac agatgagtaa atatccatct ggtgagagag tacgttatca    3300
atgtaggagc cctatgaaa tgtttgggga tgaagaagtg atgtgtttaa atggaaactg    3360
gacggaacca cctcaatgca aagattctac aggaaaatgt gggccccctc cacctattga    3420
caatggggac attacttcat tcccgttgtc agtatatgct ccagcttcat cagttgagta    3480
ccaatgccag aacttgtatc aacttgaggg taacaagcga ataacatgta gaaatggaca    3540
atggtcagaa ccaccaaaat gcttacatcc gtgtgtaata tcccgagaaa ttatggaaaa    3600
ttataacata gcattaaggt ggacagccaa acagaagctt tattcgagaa caggtgaatc    3660
agttgaattt gtgtgtaaac ggggatatcg tctttcatca cgttctcaca cattgcgaac    3720
aacatgttgg gatgggaaac tggagtatcc aacttgtgca aaaagataga atcaatcata    3780
aagtgcacac ctttattcag aactttagta ttaaatcagt tctcaatttc attttttatg    3840
tattgtttta ctccttttta ttcatacgta aaattttgga ttaatttgtg aaaatgtaat    3900
tataagctga gaccggtggc tctctt                                         3926
```

```
<210> SEQ ID NO 3
<211> LENGTH: 1231
<212> TYPE: PRT
<213> ORGANISM: Homo sapiens
<220> FEATURE:
<221> NAME/KEY: SIGNAL
<222> LOCATION: (1)...(18)
<220> FEATURE:
<221> NAME/KEY: VARIANT
<222> LOCATION: (402)...(402)
<223> OTHER INFORMATION: polymorphic residue

<400> SEQUENCE: 3
```

| Met | Arg | Leu | Leu | Ala | Lys | Ile | Ile | Cys | Leu | Met | Leu | Trp | Ala | Ile | Cys |
|---|---|---|---|---|---|---|---|---|---|---|---|---|---|---|---|
| 1 | | | | 5 | | | | | 10 | | | | | 15 | |

| Val | Ala | Glu | Asp | Cys | Asn | Glu | Leu | Pro | Pro | Arg | Arg | Asn | Thr | Glu | Ile |
|---|---|---|---|---|---|---|---|---|---|---|---|---|---|---|---|
| | | | 20 | | | | | 25 | | | | | 30 | | |

| Leu | Thr | Gly | Ser | Trp | Ser | Asp | Gln | Thr | Tyr | Pro | Glu | Gly | Thr | Gln | Ala |
|---|---|---|---|---|---|---|---|---|---|---|---|---|---|---|---|
| | | | 35 | | | | | 40 | | | | | 45 | | |

| Ile | Tyr | Lys | Cys | Arg | Pro | Gly | Tyr | Arg | Ser | Leu | Gly | Asn | Val | Ile | Met |
|---|---|---|---|---|---|---|---|---|---|---|---|---|---|---|---|
| | 50 | | | | | 55 | | | | | 60 | | | | |

| Val | Cys | Arg | Lys | Gly | Glu | Trp | Val | Ala | Leu | Asn | Pro | Leu | Arg | Lys | Cys |
|---|---|---|---|---|---|---|---|---|---|---|---|---|---|---|---|
| 65 | | | | | 70 | | | | | 75 | | | | | 80 |

| Gln | Lys | Arg | Pro | Cys | Gly | His | Pro | Gly | Asp | Thr | Pro | Phe | Gly | Thr | Phe |
|---|---|---|---|---|---|---|---|---|---|---|---|---|---|---|---|
| | | | | 85 | | | | | 90 | | | | | 95 | |

| Thr | Leu | Thr | Gly | Gly | Asn | Val | Phe | Glu | Tyr | Gly | Val | Lys | Ala | Val | Tyr |
|---|---|---|---|---|---|---|---|---|---|---|---|---|---|---|---|
| | | | 100 | | | | | 105 | | | | | 110 | | |

| Thr | Cys | Asn | Glu | Gly | Tyr | Gln | Leu | Leu | Gly | Glu | Ile | Asn | Tyr | Arg | Glu |
|---|---|---|---|---|---|---|---|---|---|---|---|---|---|---|---|
| | | | 115 | | | | | 120 | | | | | 125 | | |

| Cys | Asp | Thr | Asp | Gly | Trp | Thr | Asn | Asp | Ile | Pro | Ile | Cys | Glu | Val | Val |
|---|---|---|---|---|---|---|---|---|---|---|---|---|---|---|---|
| | 130 | | | | | 135 | | | | | 140 | | | | |

| Lys | Cys | Leu | Pro | Val | Thr | Ala | Pro | Glu | Asn | Gly | Lys | Ile | Val | Ser | Ser |
|---|---|---|---|---|---|---|---|---|---|---|---|---|---|---|---|
| 145 | | | | | 150 | | | | | 155 | | | | | 160 |

```
Ala Met Glu Pro Asp Arg Glu Tyr His Phe Gly Gln Ala Val Arg Phe
                165                 170                 175
Val Cys Asn Ser Gly Tyr Lys Ile Glu Gly Asp Glu Met His Cys
            180                 185                 190
Ser Asp Asp Gly Phe Trp Ser Lys Glu Pro Lys Cys Val Glu Ile
        195                 200                 205
Ser Cys Lys Ser Pro Asp Val Ile Asn Gly Ser Pro Ile Ser Gln Lys
    210                 215                 220
Ile Ile Tyr Lys Glu Asn Glu Arg Phe Gln Tyr Lys Cys Asn Met Gly
225                 230                 235                 240
Tyr Glu Tyr Ser Glu Arg Gly Asp Ala Val Cys Thr Glu Ser Gly Trp
                245                 250                 255
Arg Pro Leu Pro Ser Cys Glu Glu Lys Ser Cys Asp Asn Pro Tyr Ile
            260                 265                 270
Pro Asn Gly Asp Tyr Ser Pro Leu Arg Ile Lys His Arg Thr Gly Asp
        275                 280                 285
Glu Ile Thr Tyr Gln Cys Arg Asn Gly Phe Tyr Pro Ala Thr Arg Gly
    290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
                325                 330                 335
His Glu Asn Met Arg Arg Pro Tyr Phe Pro Val Ala Val Gly Lys Tyr
            340                 345                 350
Tyr Ser Tyr Tyr Cys Asp Glu His Phe Glu Thr Pro Ser Gly Ser Tyr
        355                 360                 365
Trp Asp His Ile His Cys Thr Gln Asp Gly Trp Ser Pro Ala Val Pro
    370                 375                 380
Cys Leu Arg Lys Cys Tyr Phe Pro Tyr Leu Glu Asn Gly Tyr Asn Gln
385                 390                 395                 400
Asn Tyr Gly Arg Lys Phe Val Gln Gly Lys Ser Ile Asp Val Ala Cys
                405                 410                 415
His Pro Gly Tyr Ala Leu Pro Lys Ala Gln Thr Thr Val Thr Cys Met
            420                 425                 430
Glu Asn Gly Trp Ser Pro Thr Pro Arg Cys Ile Arg Val Lys Thr Cys
        435                 440                 445
Ser Lys Ser Ser Ile Asp Ile Glu Asn Gly Phe Ile Ser Glu Ser Gln
    450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Arg Cys Gly Lys
                485                 490                 495
Asp Gly Trp Ser Ala Gln Pro Thr Cys Ile Lys Ser Cys Asp Ile Pro
            500                 505                 510
Val Phe Met Asn Ala Arg Thr Lys Asn Asp Phe Thr Trp Phe Lys Leu
        515                 520                 525
Asn Asp Thr Leu Asp Tyr Glu Cys His Asp Gly Tyr Glu Ser Asn Thr
    530                 535                 540
Gly Ser Thr Thr Gly Ser Ile Val Cys Gly Tyr Asn Gly Trp Ser Asp
545                 550                 555                 560
Leu Pro Ile Cys Tyr Glu Arg Glu Cys Glu Leu Pro Lys Ile Asp Val
                565                 570                 575
His Leu Val Pro Asp Arg Lys Lys Asp Gln Tyr Lys Val Gly Glu Val
```

-continued

```
                580             585                 590
Leu Lys Phe Ser Cys Lys Pro Gly Phe Thr Ile Val Gly Pro Asn Ser
            595                 600                 605
Val Gln Cys Tyr His Phe Gly Leu Ser Pro Asp Leu Pro Ile Cys Lys
            610                 615                 620
Glu Gln Val Gln Ser Cys Gly Pro Pro Glu Leu Leu Asn Gly Asn
625                 630                 635                 640
Val Lys Glu Lys Thr Lys Glu Glu Tyr Gly His Ser Glu Val Val Glu
                645                 650                 655
Tyr Tyr Cys Asn Pro Arg Phe Leu Met Lys Gly Pro Asn Lys Ile Gln
                660                 665                 670
Cys Val Asp Gly Glu Trp Thr Thr Leu Pro Val Cys Ile Val Glu Glu
                675                 680                 685
Ser Thr Cys Gly Asp Ile Pro Glu Leu Glu His Gly Trp Ala Gln Leu
            690                 695                 700
Ser Ser Pro Pro Tyr Tyr Tyr Gly Asp Ser Val Glu Phe Asn Cys Ser
705                 710                 715                 720
Glu Ser Phe Thr Met Ile Gly His Arg Ser Ile Thr Cys Ile His Gly
                725                 730                 735
Val Trp Thr Gln Leu Pro Gln Cys Val Ala Ile Asp Lys Leu Lys Lys
                740                 745                 750
Cys Lys Ser Ser Asn Leu Ile Ile Leu Glu Glu His Leu Lys Asn Lys
            755                 760                 765
Lys Glu Phe Asp His Asn Ser Asn Ile Arg Tyr Arg Cys Arg Gly Lys
            770                 775                 780
Glu Gly Trp Ile His Thr Val Cys Ile Asn Gly Arg Trp Asp Pro Glu
785                 790                 795                 800
Val Asn Cys Ser Met Ala Gln Ile Gln Leu Cys Pro Pro Pro Gln
                805                 810                 815
Ile Pro Asn Ser His Asn Met Thr Thr Thr Leu Asn Tyr Arg Asp Gly
                820                 825                 830
Glu Lys Val Ser Val Leu Cys Gln Glu Asn Tyr Leu Ile Gln Glu Gly
            835                 840                 845
Glu Glu Ile Thr Cys Lys Asp Gly Arg Trp Gln Ser Ile Pro Leu Cys
            850                 855                 860
Val Glu Lys Ile Pro Cys Ser Gln Pro Pro Gln Ile Glu His Gly Thr
865                 870                 875                 880
Ile Asn Ser Ser Arg Ser Ser Gln Glu Ser Tyr Ala His Gly Thr Lys
                885                 890                 895
Leu Ser Tyr Thr Cys Glu Gly Gly Phe Arg Ile Ser Glu Glu Asn Glu
                900                 905                 910
Thr Thr Cys Tyr Met Gly Lys Trp Ser Ser Pro Pro Gln Cys Glu Gly
            915                 920                 925
Leu Pro Cys Lys Ser Pro Pro Glu Ile Ser His Gly Val Val Ala His
            930                 935                 940
Met Ser Asp Ser Tyr Gln Tyr Gly Glu Glu Val Thr Tyr Lys Cys Phe
945                 950                 955                 960
Glu Gly Phe Gly Ile Asp Gly Pro Ala Ile Ala Lys Cys Leu Gly Glu
                965                 970                 975
Lys Trp Ser His Pro Pro Ser Cys Ile Lys Thr Asp Cys Leu Ser Leu
            980                 985                 990
Pro Ser Phe Glu Asn Ala Ile Pro Met Gly Glu Lys Lys Asp Val Tyr
            995                 1000                1005
```

-continued

Lys Ala Gly Glu Gln Val Thr Tyr Thr Cys Ala Thr Tyr Tyr Lys Met
    1010                1015                1020

Asp Gly Ala Ser Asn Val Thr Cys Ile Asn Ser Arg Trp Thr Gly Arg
1025                1030                1035                1040

Pro Thr Cys Arg Asp Thr Ser Cys Val Asn Pro Pro Thr Val Gln Asn
                1045                1050                1055

Ala Tyr Ile Val Ser Arg Gln Met Ser Lys Tyr Pro Ser Gly Glu Arg
                1060                1065                1070

Val Arg Tyr Gln Cys Arg Ser Pro Tyr Glu Met Phe Gly Asp Glu Glu
            1075                1080                1085

Val Met Cys Leu Asn Gly Asn Trp Thr Glu Pro Pro Gln Cys Lys Asp
    1090                1095                1100

Ser Thr Gly Lys Cys Gly Pro Pro Pro Ile Asp Asn Gly Asp Ile
1105                1110                1115                1120

Thr Ser Phe Pro Leu Ser Val Tyr Ala Pro Ala Ser Ser Val Glu Tyr
                1125                1130                1135

Gln Cys Gln Asn Leu Tyr Gln Leu Glu Gly Asn Lys Arg Ile Thr Cys
                1140                1145                1150

Arg Asn Gly Gln Trp Ser Glu Pro Pro Lys Cys Leu His Pro Cys Val
                1155                1160                1165

Ile Ser Arg Glu Ile Met Glu Asn Tyr Asn Ile Ala Leu Arg Trp Thr
    1170                1175                1180

Ala Lys Gln Lys Leu Tyr Ser Arg Thr Gly Glu Ser Val Glu Phe Val
1185                1190                1195                1200

Cys Lys Arg Gly Tyr Arg Leu Ser Ser Arg Ser His Thr Leu Arg Thr
                1205                1210                1215

Thr Cys Trp Asp Gly Lys Leu Glu Tyr Pro Thr Cys Ala Lys Arg
                1220                1225                1230

<210> SEQ ID NO 4
<211> LENGTH: 1231
<212> TYPE: PRT
<213> ORGANISM: Homo sapiens
<220> FEATURE:
<221> NAME/KEY: SIGNAL
<222> LOCATION: (1)...(18)
<220> FEATURE:
<221> NAME/KEY: VARIANT
<222> LOCATION: (402)...(402)
<223> OTHER INFORMATION: polymorphic residue

<400> SEQUENCE: 4

Met Arg Leu Leu Ala Lys Ile Ile Cys Leu Met Leu Trp Ala Ile Cys
  1               5                  10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
            115                 120                 125

```
Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
                195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
                275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
    355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn His Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
    435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Arg Cys Gly Lys
                485                 490                 495

Asp Gly Trp Ser Ala Gln Pro Thr Cys Ile Lys Ser Cys Asp Ile Pro
                500                 505                 510

Val Phe Met Asn Ala Arg Thr Lys Asn Asp Phe Thr Trp Phe Lys Leu
                515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
```

-continued

```
            545                 550                 555                 560
        Leu Pro Ile Cys Tyr Glu Arg Glu Cys Glu Leu Pro Lys Ile Asp Val
                        565                 570                 575

His Leu Val Pro Asp Arg Lys Asp Gln Tyr Lys Val Gly Glu Val
                        580                 585                 590

Leu Lys Phe Ser Cys Lys Pro Gly Phe Thr Ile Val Gly Pro Asn Ser
                        595                 600                 605

Val Gln Cys Tyr His Phe Gly Leu Ser Pro Asp Leu Pro Ile Cys Lys
                610                 615                 620

Glu Gln Val Gln Ser Cys Gly Pro Pro Glu Leu Leu Asn Gly Asn
        625                 630                 635                 640

Val Lys Glu Lys Thr Lys Glu Glu Tyr Gly His Ser Glu Val Val Glu
                        645                 650                 655

Tyr Tyr Cys Asn Pro Arg Phe Leu Met Lys Gly Pro Asn Lys Ile Gln
                        660                 665                 670

Cys Val Asp Gly Glu Trp Thr Thr Leu Pro Val Cys Ile Val Glu Glu
                        675                 680                 685

Ser Thr Cys Gly Asp Ile Pro Glu Leu Glu His Gly Trp Ala Gln Leu
                690                 695                 700

Ser Ser Pro Pro Tyr Tyr Tyr Gly Asp Ser Val Glu Phe Asn Cys Ser
        705                 710                 715                 720

Glu Ser Phe Thr Met Ile Gly His Arg Ser Ile Thr Cys Ile His Gly
                        725                 730                 735

Val Trp Thr Gln Leu Pro Gln Cys Val Ala Ile Asp Lys Leu Lys Lys
                        740                 745                 750

Cys Lys Ser Ser Asn Leu Ile Ile Leu Glu Glu His Leu Lys Asn Lys
                        755                 760                 765

Lys Glu Phe Asp His Asn Ser Asn Ile Arg Tyr Arg Cys Arg Gly Lys
                        770                 775                 780

Glu Gly Trp Ile His Thr Val Cys Ile Asn Gly Arg Trp Asp Pro Glu
        785                 790                 795                 800

Val Asn Cys Ser Met Ala Gln Ile Gln Leu Cys Pro Pro Pro Gln
                        805                 810                 815

Ile Pro Asn Ser His Asn Met Thr Thr Thr Leu Asn Tyr Arg Asp Gly
                        820                 825                 830

Glu Lys Val Ser Val Leu Cys Gln Glu Asn Tyr Leu Ile Gln Glu Gly
                        835                 840                 845

Glu Glu Ile Thr Cys Lys Asp Gly Arg Trp Gln Ser Ile Pro Leu Cys
                850                 855                 860

Val Glu Lys Ile Pro Cys Ser Gln Pro Pro Gln Ile Glu His Gly Thr
        865                 870                 875                 880

Ile Asn Ser Ser Arg Ser Ser Gln Glu Ser Tyr Ala His Gly Thr Lys
                        885                 890                 895

Leu Ser Tyr Thr Cys Glu Gly Gly Phe Arg Ile Ser Glu Glu Asn Glu
                        900                 905                 910

Thr Thr Cys Tyr Met Gly Lys Trp Ser Ser Pro Pro Gln Cys Glu Gly
                        915                 920                 925

Leu Pro Cys Lys Ser Pro Pro Glu Ile Ser His Gly Val Val Ala His
                        930                 935                 940

Met Ser Asp Ser Tyr Gln Tyr Gly Glu Glu Val Thr Tyr Lys Cys Phe
        945                 950                 955                 960

Glu Gly Phe Gly Ile Asp Gly Pro Ala Ile Ala Lys Cys Leu Gly Glu
                        965                 970                 975
```

-continued

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys Met
    1010                1015                1020

Asp Gly Ala Ser Asn Val Thr Cys Ile Asn Ser Arg Trp Thr Gly Arg
1025                1030                1035                1040

Pro Thr Cys Arg Asp Thr Ser Cys Val Asn Pro Pro Thr Val Gln Asn
                1045                1050                1055

Ala Tyr Ile Val Ser Arg Gln Met Ser Lys Tyr Pro Ser Gly Glu Arg
            1060                1065                1070

Val Arg Tyr Gln Cys Arg Ser Pro Tyr Glu Met Phe Gly Asp Glu Glu
        1075                1080                1085

Val Met Cys Leu Asn Gly Asn Trp Thr Glu Pro Pro Gln Cys Lys Asp
    1090                1095                1100

Ser Thr Gly Lys Cys Gly Pro Pro Pro Ile Asp Asn Gly Asp Ile
1105                1110                1115                1120

Thr Ser Phe Pro Leu Ser Val Tyr Ala Pro Ala Ser Ser Val Glu Tyr
                1125                1130                1135

Gln Cys Gln Asn Leu Tyr Gln Leu Glu Gly Asn Lys Arg Ile Thr Cys
            1140                1145                1150

Arg Asn Gly Gln Trp Ser Glu Pro Pro Lys Cys Leu His Pro Cys Val
        1155                1160                1165

Ile Ser Arg Glu Ile Met Glu Asn Tyr Asn Ile Ala Leu Arg Trp Thr
    1170                1175                1180

Ala Lys Gln Lys Leu Tyr Ser Arg Thr Gly Glu Ser Val Glu Phe Val
1185                1190                1195                1200

Cys Lys Arg Gly Tyr Arg Leu Ser Ser Arg Ser His Thr Leu Arg Thr
                1205                1210                1215

Thr Cys Trp Asp Gly Lys Leu Glu Tyr Pro Thr Cys Ala Lys Arg
            1220                1225                1230

<210> SEQ ID NO 5
<211> LENGTH: 23
<212> TYPE: DNA
<213> ORGANISM: Homo sapiens

<400> SEQUENCE: 5
ggtttcttct tgaaaatcac agg                                           23

<210> SEQ ID NO 6
<211> LENGTH: 22
<212> TYPE: DNA
<213> ORGANISM: Homo sapiens

<400> SEQUENCE: 6
ccattggtaa aacaaggtga ca                                            22

<210> SEQ ID NO 7
<211> LENGTH: 107
<212> TYPE: PRT
<213> ORGANISM: Homo sapiens

<400> SEQUENCE: 7

Met Leu Arg Leu Tyr Pro Gly Pro Met Val Thr Glu Ala Glu Gly Lys
1               5                   10                  15

Gly Gly Pro Glu Met Ala Ser Leu Ser Ser Ser Val Val Pro Val Ser

```
            20                  25                  30
Phe Ile Ser Thr Leu Arg Glu Ser Val Leu Asp Pro Gly Val Gly Gly
        35                  40                  45

Glu Gly Ala Ser Asp Lys Gln Arg Ser Lys Leu Ser Leu Ser His Ser
 50                  55                  60

Met Ile Pro Ala Ala Lys Ile His Thr Glu Leu Cys Leu Pro Ala Phe
 65                  70                  75                  80

Phe Ser Pro Ala Gly Thr Gln Arg Phe Gln Gln Pro Gln His His
                 85                  90                  95

Leu Thr Leu Ser Ile Ile His Thr Ala Ala Arg
            100                 105

<210> SEQ ID NO 8
<211> LENGTH: 808
<212> TYPE: DNA
<213> ORGANISM: Homo sapiens

<400> SEQUENCE: 8
gagatggcag ctggcttggc aaggggacag caccctttgtc accacattat gtccctgtac    60
cctacatgct gcgcctatac ccaggaccga tggtaactga ggcggagggg aaaggagggc   120
ctgagatggc aagtctgtcc tcctcggtgg ttcctgtgtc cttcatttcc actctgcgag   180
agtctgtgct ggaccctgga gttggtggag aaggagccag tgacaagcag aggagcaaac   240
tgtctttatc acactccatg atcccagctg ctaaaatcca cactgagctc tgcttaccag   300
ccttcttctc tcctgctgga acccagagga ggttccagca gcctcagcac cacctgacac   360
tgtctatcat ccacactgca gcaaggtgat tctgccaaaa catatctcct aaaagccaa    420
ctggagcttc tcatcagcat caatgtgaag ccaaaaatcc ttaggaggac agagggagtc   480
cctcacaacc tagactggtc cccttccctc agctgcctc aactgtccac aggactctct    540
tcccacctgc ggccacactg tgcaacctgg aatttcccca cctgggcgga ctcatcacgt   600
catcaccaat tggatgcatc ttctgctctg tgcagctggt gaaatctttc tcaacccttg   660
agatgcagcc caatcttctc ctaacatctg gattcctctc tgtcactgca ttccctcctg   720
tcatcctgcc tttgttttct tgccctcctt tctctcccgg gtgataggca ttaactaaaa   780
ttaaataaaa attcagatca tccttgca                                      808

<210> SEQ ID NO 9
<211> LENGTH: 51
<212> TYPE: DNA
<213> ORGANISM: Homo sapiens

<400> SEQUENCE: 9
tttatcacac tccatgatcc cagctkctaa aatccacact gagctctgct t            51

<210> SEQ ID NO 10
<211> LENGTH: 51
<212> TYPE: DNA
<213> ORGANISM: Homo sapiens

<400> SEQUENCE: 10
gtggaaacct cagcctgctt ctcgtycggg ttgttagagg agtcatttag a             51

<210> SEQ ID NO 11
<211> LENGTH: 51
<212> TYPE: DNA
<213> ORGANISM: Homo sapiens

<400> SEQUENCE: 11
```

-continued tttcaatatt ctcacggctt tccagkgctc attttcctg ctcatttatg g        51

<210> SEQ ID NO 12
<211> LENGTH: 51
<212> TYPE: DNA
<213> ORGANISM: Homo sapiens

<400> SEQUENCE: 12
gttagaggag tcatttagaa agctgkacca ttctttcaat attctcacgg c        51

<210> SEQ ID NO 13
<211> LENGTH: 51
<212> TYPE: DNA
<213> ORGANISM: Homo sapiens

<400> SEQUENCE: 13
ctcagcctgc ttctcgtccg ggttgktaga ggagtcattt agaaagctgt a        51

<210> SEQ ID NO 14
<211> LENGTH: 51
<212> TYPE: DNA
<213> ORGANISM: Homo sapiens

<400> SEQUENCE: 14
tccgggttgt tagaggagtc atttaraaag ctgtaccatt ctttcaatat t        51

<210> SEQ ID NO 15
<211> LENGTH: 51
<212> TYPE: DNA
<213> ORGANISM: Homo sapiens

<400> SEQUENCE: 15
taccattctt tcaatattct cacggytttc cagtgctcat ttttcctgct c        51

<210> SEQ ID NO 16
<211> LENGTH: 51
<212> TYPE: DNA
<213> ORGANISM: Homo sapiens

<400> SEQUENCE: 16
gaaactgagc agcagcaggc ctgggkttgg cttttaagta tctatattta a        51

<210> SEQ ID NO 17
<211> LENGTH: 50
<212> TYPE: DNA
<213> ORGANISM: Homo sapiens

<400> SEQUENCE: 17
catattacta aatctatttt ttttcagtc tatcatccac actgcagcaa        50

<210> SEQ ID NO 18
<211> LENGTH: 50
<212> TYPE: DNA
<213> ORGANISM: Homo sapiens

<400> SEQUENCE: 18
ttgttttctt gccctccttt ctctcccggg tgataggcat taactaaaat        50

<210> SEQ ID NO 19
<211> LENGTH: 50
<212> TYPE: DNA
<213> ORGANISM: Homo sapiens

<400> SEQUENCE: 19

```
gttttcttgc cctcctttct ctcccgggtg ataggcatta actaaaatta                50

<210> SEQ ID NO 20
<211> LENGTH: 51
<212> TYPE: DNA
<213> ORGANISM: Homo sapiens

<400> SEQUENCE: 20
ggatgcccta tctaaaaaac aaaaamcaaa aaaaaaaaag aaaaaagaaa a              51

<210> SEQ ID NO 21
<211> LENGTH: 51
<212> TYPE: DNA
<213> ORGANISM: Homo sapiens

<400> SEQUENCE: 21
ctcgagagga tgccctatct aaaaamcaaa aaacaaaaaa aaaaaagaaa a              51

<210> SEQ ID NO 22
<211> LENGTH: 51
<212> TYPE: DNA
<213> ORGANISM: Homo sapiens

<400> SEQUENCE: 22
aaaaatagta aaacaacaac aacaamaaaa aaacaacaaa aaatcccaaa a              51

<210> SEQ ID NO 23
<211> LENGTH: 50
<212> TYPE: DNA
<213> ORGANISM: Homo sapiens

<400> SEQUENCE: 23
caacctaaaa tatcgtcatg tgtctttaaa aatgcatatt actaaatcta                50

<210> SEQ ID NO 24
<211> LENGTH: 51
<212> TYPE: DNA
<213> ORGANISM: Homo sapiens

<400> SEQUENCE: 24
tttatcacac tccatgatcc cagctkctaa aatccacact gagctctgct t              51

<210> SEQ ID NO 25
<211> LENGTH: 51
<212> TYPE: DNA
<213> ORGANISM: Homo sapiens

<400> SEQUENCE: 25
tatgtccctg taccctacat gctgcrccta tacccaggac cgatggtaac t              51

<210> SEQ ID NO 26
<211> LENGTH: 51
<212> TYPE: DNA
<213> ORGANISM: Homo sapiens

<400> SEQUENCE: 26
cagatgattt caatggatac tagggwcctc tgttgcctcc tctggcagag c              51

<210> SEQ ID NO 27
<211> LENGTH: 51
<212> TYPE: DNA
<213> ORGANISM: Homo sapiens

<400> SEQUENCE: 27
```
taattcagtt ggtctggaat agtttktttt ttcctttat tttttatttt t          51

<210> SEQ ID NO 28
<211> LENGTH: 51
<212> TYPE: DNA
<213> ORGANISM: Homo sapiens

<400> SEQUENCE: 28
gactagagat gccaagcatc ttctcrtgtg tttatttgtg ctcttagagt t          51

<210> SEQ ID NO 29
<211> LENGTH: 51
<212> TYPE: DNA
<213> ORGANISM: Homo sapiens

<400> SEQUENCE: 29
acttgctgca tttcaaatgc ttggcrgtca catgtagtta gtggctaccc t          51

<210> SEQ ID NO 30
<211> LENGTH: 51
<212> TYPE: DNA
<213> ORGANISM: Homo sapiens

<400> SEQUENCE: 30
tccacaggac tctcttccca cctgcrgcca cactgtgcaa cctggaattt c          51

<210> SEQ ID NO 31
<211> LENGTH: 51
<212> TYPE: DNA
<213> ORGANISM: Homo sapiens

<400> SEQUENCE: 31
atttccccac ctgggcggac tcatcrcgtc atcaccaatt ggatgcatct t          51

<210> SEQ ID NO 32
<211> LENGTH: 51
<212> TYPE: DNA
<213> ORGANISM: Homo sapiens

<400> SEQUENCE: 32 ttttttttt cctttattt tttatwtttt tgagacagag tcttgctctg t          51

<210> SEQ ID NO 33
<211> LENGTH: 51
<212> TYPE: DNA
<213> ORGANISM: Homo sapiens

<400> SEQUENCE: 33
aaagtgctcc tcaacctaaa atatcrtcat gtgtctttaa aaatgcatat t          51

<210> SEQ ID NO 34
<211> LENGTH: 51
<212> TYPE: DNA
<213> ORGANISM: Homo sapiens

<400> SEQUENCE: 34
ggagcttctc atcagcatca atgtgmagcc aaaaatcctt aggaggacag a          51

<210> SEQ ID NO 35
<211> LENGTH: 51
<212> TYPE: DNA
<213> ORGANISM: Homo sapiens

<400> SEQUENCE: 35

```
aagccaactg agcttctca tcagcrtcaa tgtgaagcca aaaatcctta g        51

<210> SEQ ID NO 36
<211> LENGTH: 51
<212> TYPE: DNA
<213> ORGANISM: Homo sapiens

<400> SEQUENCE: 36
agcagtgcat gaggattctg atttckccac atccttgctg atacttgtta t        51

<210> SEQ ID NO 37
<211> LENGTH: 51
<212> TYPE: DNA
<213> ORGANISM: Homo sapiens

<400> SEQUENCE: 37
ggcggactca tcacgtcatc accaaytgga tgcatcttct gctctgtgca g        51

<210> SEQ ID NO 38
<211> LENGTH: 51
<212> TYPE: DNA
<213> ORGANISM: Homo sapiens

<400> SEQUENCE: 38
ccagctaatt tttgtatttt tagtasagcc aggattccac catgttagcc a        51

<210> SEQ ID NO 39
<211> LENGTH: 51
<212> TYPE: DNA
<213> ORGANISM: Homo sapiens

<400> SEQUENCE: 39
tgttgatttg ctgatgacta gagatrccaa gcatcttctc atgtgtttat t        51

<210> SEQ ID NO 40
<211> LENGTH: 51
<212> TYPE: DNA
<213> ORGANISM: Homo sapiens

<400> SEQUENCE: 40
tccaaagcag ctataccatt ttacawtccc actagcagtg catgaggatt c        51

<210> SEQ ID NO 41
<211> LENGTH: 51
<212> TYPE: DNA
<213> ORGANISM: Homo sapiens

<400> SEQUENCE: 41
agagaaagaa tctgggcctt acaggycacg ttggtttaaa atttagacat c        51

<210> SEQ ID NO 42
<211> LENGTH: 51
<212> TYPE: DNA
<213> ORGANISM: Homo sapiens

<400> SEQUENCE: 42
tttaaaaatg catattacta aatctrttttt tttttcagtc tatcatccac a        51

<210> SEQ ID NO 43
<211> LENGTH: 51
<212> TYPE: DNA
<213> ORGANISM: Homo sapiens

<400> SEQUENCE: 43
```

```
ctcgatctcc tgagctcgtg atctgyccac cttggcttcc caaagtggtg g         51
```

<210> SEQ ID NO 44
<211> LENGTH: 51
<212> TYPE: DNA
<213> ORGANISM: Homo sapiens

<400> SEQUENCE: 44

```
ttcttgccct cctttctctc ccgggkgata ggcattaact aaaattaaat a         51
```

<210> SEQ ID NO 45
<211> LENGTH: 51
<212> TYPE: DNA
<213> ORGANISM: Homo sapiens

<400> SEQUENCE: 45

```
gctgccattt aggcaaaatg gtttamcatt gaatcaagga cattatgagc c         51
```

<210> SEQ ID NO 46
<211> LENGTH: 51
<212> TYPE: DNA
<213> ORGANISM: Homo sapiens

<400> SEQUENCE: 46

```
tcaaacagag ccccaggcag ccaccraaag gtcttgaatg acagcttgtc a         51
```

<210> SEQ ID NO 47
<211> LENGTH: 51
<212> TYPE: DNA
<213> ORGANISM: Homo sapiens

<400> SEQUENCE: 47

```
ccttcccta aatcagttgc atgagrccag cagtccatct ttgcattaat t          51
```

<210> SEQ ID NO 48
<211> LENGTH: 51
<212> TYPE: DNA
<213> ORGANISM: Homo sapiens

<400> SEQUENCE: 48

```
atgcaactga tttaggggaa gggttygcct aaattaataa aagatctgaa t         51
```

<210> SEQ ID NO 49
<211> LENGTH: 51
<212> TYPE: DNA
<213> ORGANISM: Homo sapiens

<400> SEQUENCE: 49

```
tcctgtgtcc ttcatttcca ctctgygaga gtctgtgctg gaccctggag t         51
```

<210> SEQ ID NO 50
<211> LENGTH: 51
<212> TYPE: DNA
<213> ORGANISM: Homo sapiens

<400> SEQUENCE: 50

```
tttctctccc gggtgatagg cattamctaa aattaaataa aaattcagat c         51
```

<210> SEQ ID NO 51
<211> LENGTH: 51
<212> TYPE: DNA
<213> ORGANISM: Homo sapiens

<400> SEQUENCE: 51

-continued

```
ttgccctcct ttctctcccg ggtgayaggc attaactaaa attaaataaa a          51

<210> SEQ ID NO 52
<211> LENGTH: 51
<212> TYPE: DNA
<213> ORGANISM: Homo sapiens

<400> SEQUENCE: 52
ctgaggtggg aggatcacct gagccsagga gtatgaggct gcagtgagcc a          51

<210> SEQ ID NO 53
<211> LENGTH: 51
<212> TYPE: DNA
<213> ORGANISM: Homo sapiens

<400> SEQUENCE: 53
catattacta aatctatttt tttttttcagt ctatcatcca cactgcagca a         51

<210> SEQ ID NO 54
<211> LENGTH: 51
<212> TYPE: DNA
<213> ORGANISM: Homo sapiens

<400> SEQUENCE: 54
ttgttttctt gccctccttt ctctctccgg gtgataggca ttaactaaaa t          51

<210> SEQ ID NO 55
<211> LENGTH: 51
<212> TYPE: DNA
<213> ORGANISM: Homo sapiens

<400> SEQUENCE: 55
gttttcttgc cctcctttct ctccctgggt gataggcatt aactaaaatt a         51

<210> SEQ ID NO 56
<211> LENGTH: 52
<212> TYPE: DNA
<213> ORGANISM: Homo sapiens

<400> SEQUENCE: 56
caacctaaaa tatcgtcatg tgtctattta aaaatgcata ttactaaatc ta        52
```

GENETIC VARIANTS INCREASE THE RISK OF AGE-RELATED MACULAR DEGENERATION

This invention was made using funds from U.S. government grant no.U10EY012118. and EY015216 from the National Institutes of Health (NIH)/National Eye Institute and by grant AG11268 from the NIH/National Institute on Aging and by RR 00095 from the National Institutes of Health GCRC. Therefore the U.S. government retains certain rights in the invention.

TECHNICAL FIELD OF THE INVENTION

This invention is related to the area of genetic testing, drug discovery, and Age-Related Macular Degeneration. In particular, it relates to genetic variants which increase the risk of Age-Related Macular Degeneration, particularly in combination with certain behavior.

BACKGROUND OF THE INVENTION

Age-related macular degeneration (AMD) causes progressive impairment of central vision and is the leading cause of irreversible vision loss in older Americans (1). The most severe form of AMD involves neovascular/exudative (wet) and/or atrophic (dry) changes to the macula. Although the etiology of AMD remains largely unknown, implicated risk factors include age, ethnicity, smoking, hypertension, obesity and diet (2). Familial aggregation (3), twin studies (4), and segregation analysis (5) suggest that there is also a significant genetic contribution to the disease. The candidate gene approach, which focuses on testing biologically relevant candidates, has implicated variants in the ABCA4, FBLN6, and APOE genes as risk factors for AMD. Replication of the ABCA4 and FBLN6 findings has been difficult, and in toto these variants explain only a small proportion of AMD (6-8). An alternative genomic approach uses a combination of genetic linkage and association to identify novel genes involved in AMD. We participated in a recent collaborative genome-wide linkage screen (9) in which chromosome 1q32 was identified as a likely region for an AMD risk gene, a location also supported by other studies (10, 11). This region contains between over 100 genes, (see On-line Mendelian Inheritance in Man at the NCBI website) and no particular gene was identified by this work.

Age-related macular degeneration (AMD) is a common complex disorder that affects the central region of the retina (macula) and is the leading cause of legal blindness in older American adults. The prevalence of AMD and its significant morbidity will rise sharply as the population ages. AMD is a clinically heterogeneous disorder with a poorly understood etiology. Population-based longitudinal studies (Klayer et al. 2001; van Leeuwen et al. 2003; Klein et al. 2003) have established that the presence of extracellular protein/lipid deposits (drusen) between the basal lamina of the retinal pigment epithelium (RPE) and the inner layer of Bruchs' membrane is associated with an increased risk of progressing to an advanced form of AMD, either geographic atrophy or exudative disease. The presence of large and indistinct (soft) drusen coupled with RPE abnormalities is considered an early form of the disorder and is often referred to as age-related maculopathy (ARM).

Epidemiologically, AMD is a complex disorder with contributions of environmental factors as well as genetic susceptibility (Klein et al. 2004). Many environmental and lifestyle factors have been postulated, but by far the most consistently implicated non-genetic risk factor for AMD is cigarette smoking (Smith et al. 2001). Much progress has recently been made in identifying and characterizing the genetic basis of AMD. In a remarkable example of the convergence of methods for disease gene discovery, multiple independent research efforts identified the Y402H variant in the complement factor H(CFH [(MIM 134370]) gene on chromosome 1q32 as the first major AMD susceptibility allele (Haines et al. 2005; Hageman et al. 2005; Klein et al. 2005; Edwards et al. 2005; Zareparsi et al. 2005; Conley et al. 2005). While one of the studies was able to pinpoint CFH on the basis of a whole-genome association study (Klein et al. 2005), most studies focused on the 1q32 region because it had consistently been implicated by several whole-genome linkage scans. A second genomic region with similarly consistent linkage evidence is chromosome 10q26, which was identified as the single most promising region by a recent meta-analysis of published linkage screens (Fisher et al. 2005).

Two recent studies have suggested specific AMD susceptibility genes located on chromosome 10q26. One used a combination of family-based and case-control analyses to implicate the PLEKHA1 gene (pleckstrin homology domain containing, family A (phosphoinositide binding specific) member 1 [MIM 607772]) and the predicted LOC387715 gene (Jakobsdottir et al. 2005). However, the association signals for single-nucleotide polymorphisms (SNPs) in these two genes were statistically indistinguishable. A second study using two independent case-control datasets concluded that the T allele of SNP rs10490924 in LOC387715, a coding change (Ala69Ser) in exon 1 of this poorly characterized gene, was the most likely AMD susceptibility allele (Rivera et al. 2005). Both studies reported that the chromosome 10q26 variant confers an AMD risk similar in magnitude to that of the Y402H variant in CFH. Here, we describe highly significant association of SNPs in LOC387715 with AMD. In our data, only SNPs in this gene, including rs10490924, explain the strong linkage and association signal in this region. Given a previous report of an effect of cigarette smoking on the linkage evidence in the 10q26 region (Weeks et al. 2004; 9), we tested whether smoking modified this association.

There is a continuing need in the art to identify individual genes that are involved in the pathogenesis of AMD and/or to identify particular alleles that are involved in the pathogenesis of AMD, as well as to identify the interaction of the genes with modifiable behaviors.

SUMMARY OF THE INVENTION

According to one embodiment of the invention a method is provided for assessing increased risk of Age Related Macular Degeneration. The identity is determined of at least one nucleotide residue of Complement Factor H coding sequence of a person. The nucleotide residue is identified as normal or variant by comparing it to a normal sequence of Complement Factor H coding sequence as shown in SEQ ID NO: 1. A person with a variant sequence has a higher risk of Age Related Macular Degeneration than a person with a normal sequence.

According to another embodiment a method is provided for assessing increased risk of Age Related Macular Degeneration. The identity is determined of at least one amino acid residue of Complement Factor H protein of a person. The residue is identified as normal or variant by comparing it to a normal sequence of Complement Factor H as shown in SEQ ID NO: 2. A person with a variant sequence has a higher risk of Age Related Macular Degeneration than a person with a normal sequence.

Another embodiment of the invention provides a method for screening for a potential drug for treating Age Related Macular Degeneration. A Complement Factor H protein is contacted with a test agent in the presence of a polyanion. Binding of the polyanion to Complement Factor H is measured. A test agent is identified as a potential drug for treating Age Related Macular Degeneration if it increases binding of Complement Factor H to the polyanion.

Another embodiment of the invention is a method for screening for a potential drug for treating Age Related Macular Degeneration. A Complement Factor H protein is contacted with a test agent in the presence of C-Reactive Protein. C-Reactive Protein binding to Complement Factor H is measured. A test agent is identified as a potential drug for treating Age Related Macular Degeneration if it increases binding of Complement Factor H to C-Reactive Protein.

A further embodiment of the invention is a method to assess risk of AMD in a patient. The presence of a T allele at rs10490924 is determined in a patient. Whether the patient is a cigarette smoker is determined. The patient is identified as being at high risk of AMD if the patient has the T allele and is a cigarette smoker. The patient is identified as being at lower risk of AMD if the patient has the T allele but is not a cigarette smoker or is a cigarette smoker but does not have the T allele. The patient is identified as being at lowest risk if the patient does not have the T allele and is not a cigarette smoker.

Yet another embodiment of the invention is a method to assess risk and treat AMD in a patient. The presence of a T allele at rs10490924 is determined in a patient. Whether the patient is a cigarette smoker is determined. If the patient has the T allele at rs10490924 and is a cigarette smoker, behavioral therapy is provided to the patient to encourage smoking cessation.

Still another embodiment of the invention is a method to assess risk and treat AMD in a patient. The presence of a T allele at rs10490924 is determined in a patient. Whether the patient is a cigarette smoker is determined. If the patient has the T allele at rs10490924 and is a cigarette smoker, the patient is provided with smokeless nicotine to encourage smoking cessation.

BRIEF DESCRIPTION OF THE DRAWINGS

FIG. 7: Table 4. Demographic and clinical characteristics of study population

FIG. 8: Table 5. SNPs in 122-127 Mb region with ≦0.005 in case-control association analysis. MAF: minor allele frequency. Odds ratios (OR) adjusted for age and sex, estimated separately for heterozygous (het) and homozygous (het) carriers of minor allele. P-value from additive coding of SNP covariate described in text. GIST: Genotype-IBD sharing test (Li et al. 2004).

FIG. 9: Table 6. Two-locus genotype frequencies (%) and odds ratios for rs10490924 in LOC387715 and Y402H in CFH. All odds ratios adjusted for age and sex.

FIG. 10: Table 7. Results of fitting two-factor models by logistic regression, adjusted for age and sex. Factor 1 is rs10490924, model definitions in text. Akaike's information criterion (AIC) difference is difference of the AIC from the best-fitting model.

FIG. 11 Table 8. Joint frequencies (%) and odds ratios for rs10490924 in LOC387715 and smoking history (ever vs. never). All odds ratios adjusted for age and sex.

FIG. 12: Table 9. Minor allele frequency (MAF) and genotype frequencies (number of individuals) at rs10490924 by AMD grade. Data for smokers and non-smokers estimated from dataset used for logistic regression modeling (Table 8). Data for all genotyped individuals estimated by combining family-based and case-control dataset, including related individuals.

FIG. 13: Supplemental Table 1. SNPs identified in LOC387715 sequencing of individuals homozygous for rs10490924 variant FIG. 14: Supplemental Table 2. SNPs identified in CUZD1 sequencing of individuals homozygous for rs1891110 variant FIG. 15: Supplemental Table 3. Case-control association results for all SNPs in 112-132 Mb region.

DETAILED DESCRIPTION OF THE INVENTION

Figure 1:
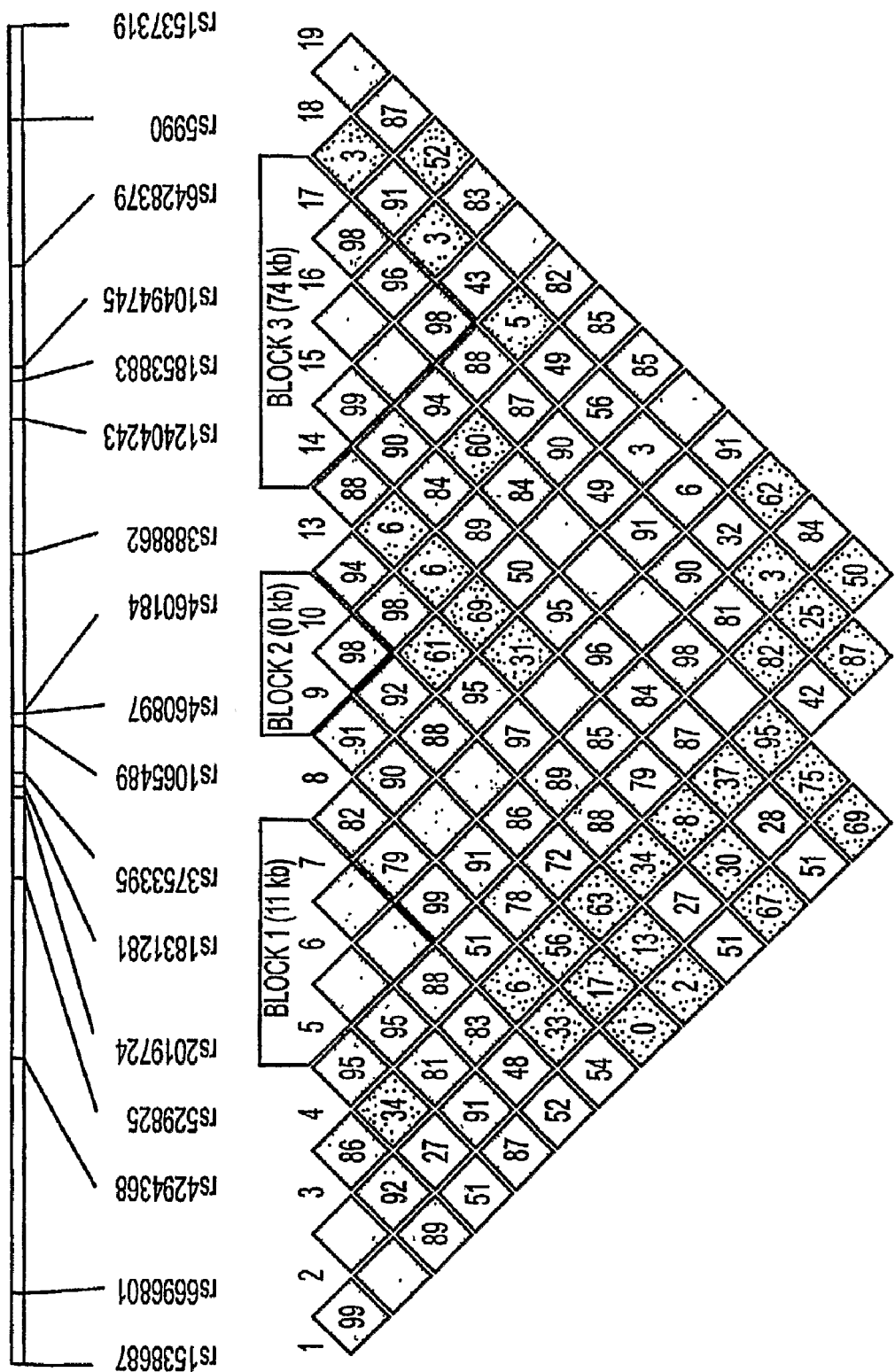
FIG. 1. Haploview plot defining haplotype block structure of AMD associated region. The relative physical position of each SNP is given in the upper diagram, and the pairwise linkage disequilibrium (D') between all SNPs is given below each SNP combination. Dark red shaded squares indicated D' values >0.80. D'=1.0 when no number is given.

The inventors have developed methods for assessing risk of developing Age-Related Macular Degeneration (AMD) in affected families and in individuals not known to be in affected families. Although developing the disease is a multifactorial process, presence of a polymorphism in the CFH gene (or complement factor H protein) indicates a greatly increased risk (approximately double). Interestingly, one polymorphism is so prevalent in the Caucasian population that ⅓ of individuals carry at least one copy of that form. Moreover, identification of the CFH gene as involved in AMD pathogenesis permits the use of the CFH protein in drug screening assays. In addition, we have identified a coding change (Ala69Ser) in the LOC387715 gene as a second major susceptibility allele for AMD. The overall effect of the gene on risk is driven by a highly significant statistical interaction between the LOC387715 variant and cigarette smoking.

The Y402H polymorphism (encoded by the T1277C polymorphism) is located in the domain known as SCR7. See Table 3. SCR7 is known to contain binding sites for both C-Reactive Protein (CRP) and polyanions, such as heparin and sialic acid. The location of this highly informative polymorphism suggests that not only is the CFH protein involved in the pathogenesis of AMD, but that the ability to bind one or both of C-Reactive protein and polyanions is also involved. Variations in other domains of CFH may also relate to pathogenesis of AMD, including variations in domains that are involved in binding of complement factor C3b. Such variations may have an effect alone or in conjunction with the Y402H variant.

Any change in the CFH gene or encoded protein can be determined by comparing to the sequences of the major allele in the Caucasian population as shown in SEQ ID NO: 1 and 3, for nucleotide and protein, respectively. Methods of detecting sequence differences between a test subject's CFH and the major allele or major protein can be any method known in the art. These include side-by-side comparisons of physicochemical properties of proteins, immunological assays, primer extension methods, hybridization methods, nucleotide sequencing, amino acid sequencing, hybridization, amplification, PCR, oligonucleotide mismatch ligation assays, primer extension assays, heteroduplex analysis, allele-specific amplification, allele-specific primer extension, SCCP, DGGE, TGCE, mass spectroscopy, high pressure liquid chromatography, and combinations of these techniques.

Binding assays between Complement Factor H and either polyanions or C-Reactive Protein (CRP) can be performed using any format known in the art. Binding can be measured in solution or on a solid support. One of the partners may, for example, be labeled with a radiolabel or fluorescent label. Partners can be identified using first antibodies which are either themselves labeled or measured using second antibodies which are labeled and reactive with the first antibodies. Assay formats can be competitive or non-competitive.

Test agents can be natural products or synthetic, purified or mixtures. They can be the products of combinatorial chemistry or individual products or families of products which are selected on the basis of structural information. Test agents are identified as candidates for treating AMD if they increase the binding of complement factor H to any of its physiological binding partners, including but not limited to C3b, sialic acid, heparin, and CRP.

The T allele is the variant of rs10490924 that has a T at nucleotide 26 as shown in SEQ ID NO: 9. Other variant alleles as shown in SEQ ID NO: 7-56 can be detected and used to assess risk of AMD. The other variants may be used independently or may be used in conjunction with an assessment of smoker status. Current smokers are individuals who smoke at least once per week. However, historical smoking in an individual's past can also modify their risk of AMD.

Behavioral therapies which can be recommended for smoking cessation include but are not limited to counseling, classes, printed information, electronic information, video or audio tapes. Providing a behavioral therapy may involve merely recommending it to a patient, prescribing it, or actually delivering the therapy. Smokeless nicotine is also a possible means for weaning persons from a smoking habit. Smokeless nicotine, like behavioral therapies, may or may not require a physician's prescription. Smokeless forms of nicotine that can be used for smoking cessation or abatement include but are not limited to nicotine gums, transdermal patches, nasal sprays, and inhalers.

Because the data indicate that the variant of CFH and the variant of LOC387715 are independent predictive factors, they can both be assessed in the same person. Together, these two types of variants are believed to account for the majority of cases of AMD. Additional factors as discovered can also be tested, as they become available to the art.

Using iterative high-density SNP association mapping, we have identified a coding change in the LOC387715 gene, at SNP rs10490924, as the most likely second major AMD susceptibility allele. We also generated statistical evidence of gene-environment interaction for this variant, suggesting that a genetic susceptibility coupled with a modifiable lifestyle factor such as cigarette smoking confers a significantly higher risk of AMD than either factor alone. Genotype frequencies at rs10490924 were strongly correlated with pack-years of smoking in AMD patients, consistent with heterogeneity analysis of the genetic linkage data. It is striking that we have observed evidence for gene-environment interaction in two different datasets using two statistically independent approaches. However, the presence of statistical interaction does not prove biological interaction, and much work remains to be done to identify the molecular mechanism underlying the increased AMD risk.

Our data did not support the previously reported association of AMD with the GRK5/RGS10 region at ~121 Mb (Jakobsdottir et al. 2005) since the four SNPs (hcv1809962, rs871196, rs1537576, rs1467813) that we genotyped in this region did not demonstrate significant association (p>0.05). The GIST and conditional haplotype analyses suggested that only rs10490924, and surrounding SNPs in LOC387715 in high LD with it, explained the linkage and association signals in this region. See other SNPs in LOC387715 at SEQ ID NO: 7-56. Neither analysis supported SNPs in the nearby PLEKHA1 and PRSS11 genes as being responsible for either the linkage or association evidence. Consistent with these results, the most significant single-SNP associations, the highest odds ratios, and the highest nonparametric two-point lod score of 3.2 were contributed by SNPs in the LOC387715 gene. While we did not re-sequence the nearby PLEKHA1 and PRSS11 genes, we genotyped the vast majority of SNPs examined by the earlier studies in our dataset. Several SNPs in the CUZD1 gene, which is not in LD with the PLEKHA1/LOC387715 LD block, gave substantial association signals with logistic regression (smallest p-value: 0.0002), but allele frequency differences in cases and controls were much less pronounced for these SNPs ($MAF_{cases}$~55%, $MAF_{controls}$~48%), compared to SNPs in LOC387715 ($MAF_{cases}$~41%, $MAF_{controls}$~26%). In addition, the GIST method and the conditional haplotype analysis suggested that these SNPs did not explain the linkage and association signals in this region.

The limitations of any retrospective epidemiologic study apply to our findings, including the potential for recall bias of past exposures. The validity of the summary PAR % estimates depends on the extent to which our case-control dataset is representative of a population-based sample of AMD patients and controls. Since our dataset was used to identify the LOC387715 susceptibility variant, it is possible that its effect size, and hence its PAR %, was overestimated (Lohmueller et al. 2003; Ioannidis et al. 2001). Independent population-based studies of large sample size, ideally collected in a prospective fashion, are needed to confirm the statistical interaction between smoking and rs10490924 in contributing to AMD and its clinical subtypes, and to refine estimates of their individual and joint PAR %.

There is currently no biological explanation for the mechanism by which LOC387715 may increase the risk of AMD. It is not clear whether this statistical association provides further support to the role of the innate immunity system that was highlighted by the recent discovery of the CFH gene. LOC387715 is a two-exon gene that encodes a protein of 107 amino acids, whose only homologue is a chimpanzee gene of 97% protein identity. No significant matches were found with any known protein motifs. ESTs have been recovered from the placenta and the testis, and this gene has recently been reported to be weakly expressed in the retina (Rivera et al. 2005).

In summary, we have replicated and refined previous reports implicating a coding change in LOC387715 as the second major AMD susceptibility allele. The effect of rs10490924 appears to be completely independent of the Y402H variant in the CFH gene. The joint effect of these two susceptibility genes is consistent with a multiplicative model, and together, they may explain as much as 65% of the PAR of AMD. Previous data by our group suggested that the joint effects of CFH and smoking are also consistent with a multiplicative model (Scott et al. 2005). In contrast, the effect of rs10490924 appears to be strongly modified by cigarette smoking. Smoking and LOC387715 together may explain as much as 34% of AMD. While the marginal effect of rs10490924 was strong enough to be detected without incorporating smoking history information, an effect modification of a genetic susceptibility by a lifestyle factor like smoking has important implications for the clinical interpretation of this finding. Our data suggest that the T allele at rs10490924 may only moderately increase the AMD risk in non-smokers and likely exerts its strongest effect on heavy smokers. This has the potential to reduce the impact of an AMD susceptibility allele on the aging population by public health efforts, such as smoking prevention and smoking cessation programs. Our replication of the 10q26 linkage heterogeneity due to smoking, and the consistency of results from multiple statistically independent approaches for assessing gene-environment interaction reported here, are unusual in genetic studies of complex human diseases and provide substantial support to our findings.

We used iterative association mapping to identify a susceptibility gene for age-related macular degeneration (AMD) on chromosome 10q26, which is one of the most consistently implicated linkage regions for this disorder. We employed linkage analysis methods, followed by family-based and case-control association analysis using two independent datasets. To identify statistically the most likely AMD susceptibility allele, we used the Genotype-IBD Sharing Test (GIST) and conditional haplotype analysis. To incorporate the two most important known AMD risk factors, smoking and the Y402H variant of the complement factor H (CFH) gene, we used logistic regression modeling to test for gene-gene and gene-environment interaction in the case-control dataset, and the ordered subset analysis (OSA) to account for genetic linkage heterogeneity in the family-based dataset. Our results strongly implicate a coding change (Ala69Ser) in the LOC387715 gene as the second major AMD susceptibility allele, confirming earlier suggestions. Its effect on AMD is statistically independent of CFH and of similar magnitude to Y402H. The overall effect is driven primarily by a strong association in smokers, as we observed significant evidence for a statistical interaction of the LOC387715 variant with a history of cigarette smoking. This gene-environment interaction is supported by statistically independent family-based and case-control analysis methods. We estimate that LOC287715 and smoking together explain 34% of the population-attributable risk (PAR) of AMD. Further, we estimate that LOC387715 and CFH together account for 65% of the PAR of AMD. For the first time, we demonstrate that a genetic susceptibility coupled with a modifiable lifestyle factor such as cigarette smoking confers a significantly higher risk of AMD than either factor alone.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

To identify the responsible gene on chromosome 1q32, we initially genotyped 44 SNPs (12) across the 24 megabases (Mb) incorporating this linkage region. We examined two independent data sets: the first contained 182 families (111 multiplex and 71 discordant sibpairs) and the second contained 495 AMD cases and 185 controls. Each SNP was tested for association independently in both data sets. Two SNPs (rs2019724 and rs6428379) in moderate linkage disequilibrium with each other ($r^2$=0.61) generated highly significant associations with AMD in both the family-based data set (rs2019724, P=0.0001; rs6428379, P=0.0007) and in the case-control data set (rs2019724, P<0.0001; rs6428379, P<0.0001). These SNPs lie approximately 263 kilobases (Kb) apart.

EXAMPLE 2

Figure 2:
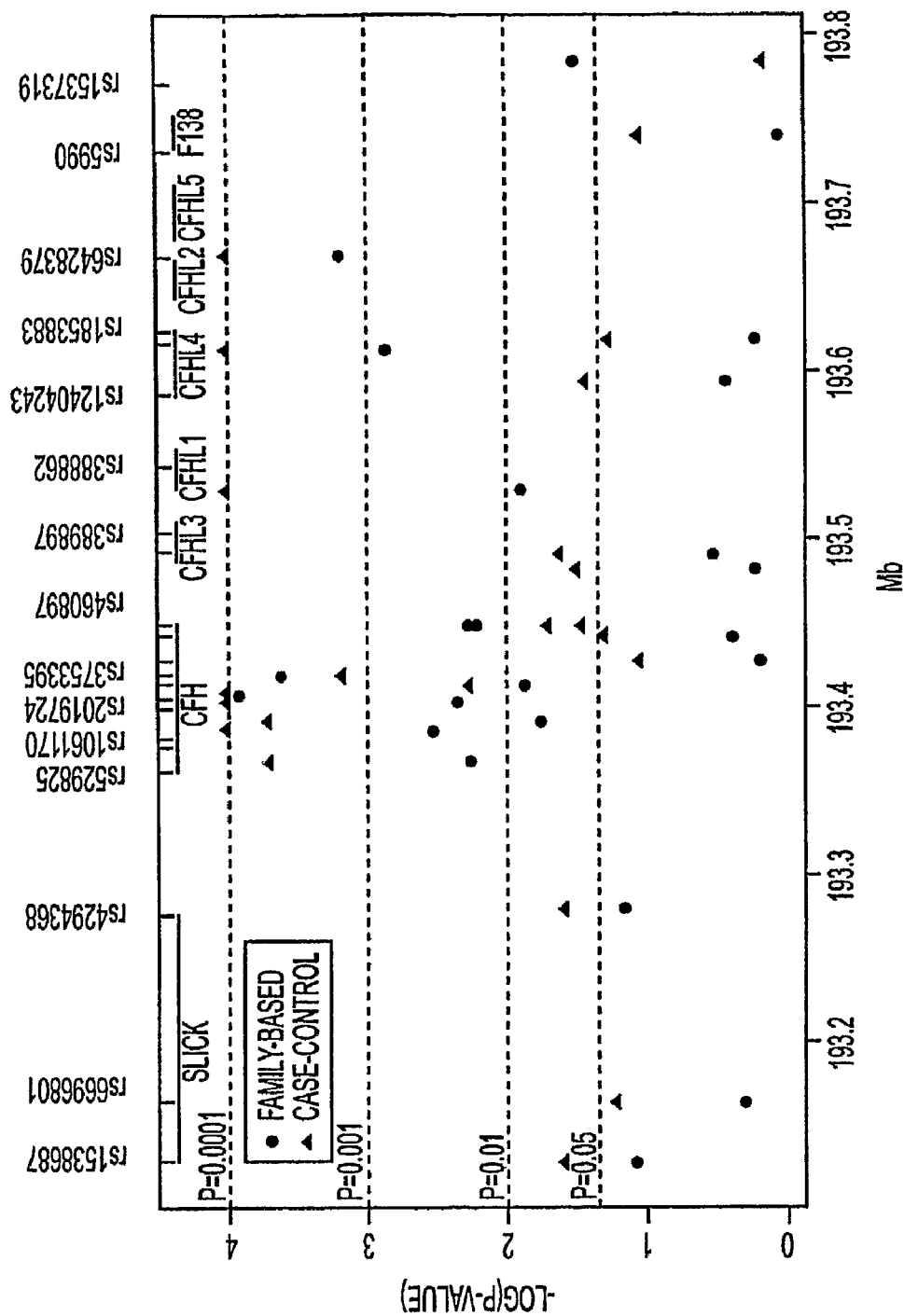
FIG. 2. Plot of family-based and case-control P values for all SNPs within the AMD-associated haplotype. The genomic region spanning each gene is indicated in green. $-\log_{10}$ of the nominal P values are plotted for each SNP. Results for both the family-based and case-control data sets converge within the CFH gene.

To define the extent of linkage disequilibrium completely, an additional 17 SNPs were genotyped across approximately 655 Kb flanked by rs1538687 and rs1537319 and encompassing the 263 Kb region. Two linkage disequilibrium blocks of 11 Kb and 74 Kb were identified and were separated by 176 Kb (FIG. 1). The 11 Kb block contained rs2019724 and the 74 Kb block contained rs6428379. Association analysis of the 17 SNPs identified multiple additional SNPs giving highly significant associations in one or both of the family-based and case-control data sets (FIG. 2). In the case-control data set, a five SNP haplotype (GAGGT, defined by SNPs rs1831281, rs3753395, rs1853883, rs10494745, and rs6428279, respectively) comprised 46% of the case and 33% of the control chromosomes (P=0.0003). This same haplotype was also significantly over-transmitted to affected individuals in the family-based data set (P=0.00003). The convergence of the most significant associations to this same haplotype in the two independent data sets strongly suggests that this region contains a commonly inherited variant in an AMD risk gene.

The associated GAGGT haplotype spans approximately 261 Kb. It contains the Complement Factor H gene (CFH, OMIM #:134370, Accession #:NM_000186) and the five Factor H-related genes CFHL1-5, and lies within the Regulator of Complement Activation (RCA) gene cluster. The most consistent association results (FIG. 2) from both the family-based and case-control data sets converge within the CFH gene implicating CFH as the AMD susceptibility gene. The biological role of Complement Factor H as a component of the innate immune system that modulates inflammation through regulation of complement (reviewed in (13)) enhances its attractiveness as a candidate AMD susceptibility gene. Inflammation has been repeatedly implicated in AMD pathology. C-reactive protein levels are elevated in advanced disease (14), anti-retinal autoantibodies have been detected in AMD patients (15), macrophages are localized near neovascular lesions (16), and the hallmark drusen deposits contain many complement-related proteins (17).

EXAMPLE 3

We screened for potential risk-associated sequence variants in the coding region of CFH by sequencing 24 cases with severe neovascular disease and 24 controls with no evidence of AMD. To maximize the likelihood of identifying the risk-associated allele, all sequenced cases and controls were homozygous for the GAGGT haplotype. Five novel and six known sequence variants were detected (Table 1). Only one variant (rs1061170, sequence: T1277C, protein: Y402H) was present significantly more often in cases than controls, occurring on 45/48 haplotypes in the cases and on 22/48 haplotypes in the controls (P<0.0001). The frequency of sequence variants within the CFH coding region on the associated haplotype was significantly reduced in cases compared to controls (12% vs. 18%, P=0.002). When the over-represented T1277C variant was removed from the analysis, this difference became more pronounced (3% vs. 16%, P<0.00001). Thus T1277C is the primary DNA sequence variant differentiating between the case and control haplotypes.

TABLE 1

CFH sequence variants identified in neovascular AMD cases and normal controls.

| Location | SNP ID | effect | Minor Allele Frequency (%) | |
|---|---|---|---|---|
| | | | AMD | Controls |
| exon 1 | rs3753394 | n/a | 18 | 24 |
| exon 2 | rs800292 | V62I | 0 | 6 |
| exon 6 | 193,380,486 A/G | R232R | 0 | 2 |
| exon 7 | rs1061147 | A307A | 10 | 38 |
| exon 8 | 193,390,164 C/T | H332Y | 0 | 5 |
| exon 9 | rs1061170 | Y402H | 94 | 46 |
| exon 11 | 193,414,604 A/G | A473A | 0 | 31 |
| exon 12 | 193,416,415 A/G | T519A | 0 | 2 |
| exon 14 | rs3753396 | Q672Q | 0 | 23 |
| exon 18 | 193,438,299 C/T | H878H | 6 | 2 |
| exon 19 | HGVbase 000779895 | E936D | 0 | 23 |

All individuals were homozygous for the AMD-associated GAGGT haplotype.
The 24 affected individuals selected for sequencing had severe neovascular disease (grade 5) (12) with diagnosis before age 74 (mean age at diagnosis: 65.8 yrs).
The 24 control individuals selected for sequencing had no evidence of AMD (grade 1) with age at exam after age 64 (mean age at exam: 69.8 yrs).
The six previously identified SNPs are labeled using standard nomenclature.
The five novel variants are labeled given their base pair location on chromosome 1, Ensembl build 35.
Five SNPs create non-synonymous amino acid changes within CFH and five SNPs create synonymous changes. Exon 1 is not translated.

EXAMPLE 4

We screened for potential risk-associated sequence variants in the coding region of CFH by sequencing 24 cases with severe neovascular disease and 24 controls with no evidence of AMD. To maximize the likelihood of identifying the risk-associated allele, all sequenced cases and controls were homozygous for the GAGGT haplotype. Five novel and six known sequence variants were detected (Table 1). Only one variant (rs1061170, sequence: T1277C, protein: Y402H) was present significantly more often in cases than controls, occurring on 45/48 haplotypes in the cases and on 22/48 haplotypes in the controls (P<0.0001). The frequency of sequence variants within the CFH coding region on the associated haplotype was significantly reduced in cases compared to controls (12% vs. 18%, P=0.002). When the over-represented T1277C variant was removed from the analysis, this difference became more pronounced (3% vs. 16%, P<0.00001). Thus T1277C is the primary DNA sequence variant differentiating between the case and control haplotypes.

EXAMPLE 5

Complete genotyping of T1277C in the family-based and case-control data sets revealed a significant over-transmission in the families (P=0.019) (12) and a highly significant over-representation in the cases compared to controls (P=0.00006). The odds ratio for AMD was 2.45 (95% CI: 1.41-4.25) for carriers of one C allele and 3.33 (95% CI: 1.79-6.20) for carriers of two C alleles. When the analysis was restricted to only neovascular AMD, these odds ratios increased to 3.45 (95% CI: 1.72-6.92) and 5.57 (95% CI: 2.52-12.27), respectively. This apparent dose effect for risk associated with the C allele was highly significant (P<0.0001). There was no apparent allelic or genotypic effect of T1277C on age at AMD diagnosis (mean age at diagnosis: TT: 76.5 yrs; TC 77.5 yrs; CC 75.5 yrs). The population attributable risk percent for carrying at least one C allele was 43% (95% confidence interval 23-68%).

The Y402H variant is predicted to have functional consequences consistent with AMD pathology. Residue 402 is located within binding sites for heparin (18) and C-reactive protein (CRP) (19). Binding to either of these partners increases the affinity of CFH for the complement protein C3b (20, 21), augmenting its ability to down-regulate complement's effect. The observed co-localization of CFH, CRP, and proteoglycans in the superficial layer of the arterial intima suggests that CFH may protect the host arterial wall from excess complement activation (22). We hypothesize that allele-specific changes in the activities of the binding sites for heparin and CRP would alter CFH's ability to suppress complement-related damage to arterial walls, and might ultimately lead to vessel injury and subsequent neovascular/exudative changes such as those seen in neovascular AMD. Our data support this hypothesis since the risk associated with the C allele is more pronounced when the analyses are restricted to neovascular AMD. Given the known functional interactions of genes within the RCA gene cluster (13), variants within these genes could interact with or modify the effect of the T1277C variant.

Interestingly, plasma levels of CFH are known to decrease both with age and with smoking (23), two known risk factors for AMD (2). This confluence of genetic and environmental risk factors suggests an integrated etiological model of AMD involving chronic inflammation. Identification of the increased risk of AMD associated with the T1277C variant should enhance our ability to develop presymptomatic tests for AMD, possibly allowing earlier detection and better treatment of this debilitating disorder.

EXAMPLE 6

Relates to Examples 1-5

Participants

We ascertained AMD patients and their affected and unaffected family members through two clinics in the Southeastern United States—Duke University Medical Center (DUMC) and Vanderbilt University Medical Center (VUMC). Unrelated controls of similar age and ethnic background were enrolled via (i) study advertisement in DUMC- and VUMC-affiliated newsletters; (ii) recruitment presentations by study coordinators at local retirement communities, who were likely to obtain health care at DUMC or VUMC, respectively; (iii) AMD-related seminars for the general public sponsored by DUMC or VUMC opthalmology clinics. (iv) referrals from other clinics in the Duke and Vanderbilt Eye Centers of individuals without evidence of ocular disease. Spouses of AMD patients were also asked to participate as potential controls. Controls eligible for enrollment were offered a free comprehensive eye exam including fundus photography to ensure that the same methodology was used to assign AMD grades as for the AMD patients and their relatives ascertained in clinic. All cases and controls included in this study were Caucasian and at least 55 years of age. The study protocol was approved by the respective Institutional Review Boards (IRB) at DUMC and VUMC, and the research adhered to the tenets of the Declaration of Helsinki.

The family-based data set consisted of 111 multiplex families with at least two individuals with grade 3 or higher AMD in at least one eye. Seventy-three families had two affected individuals, 29 families had three affected individuals, and nine families had four or more affected individuals. Unaffected spouses and siblings were collected whenever possible. 71 additional families consisted of one affected individual and at least one unaffected sibling (discordant sibpairs).

Clinical Assessment

The assignment of AMD affection status was based on the clinical evaluation of stereoscopic color fundus photographs of the macula (EAP, AA), according to a 5-grade system described previously (S1). Grade 1 has no AMD features, grade 2 has only small non-extensive drusen, grade 3 has extensive intermediate and/or large drusen, grade 4 is geographic atrophy, and grade 5 is neovascular AMD. This system is a slight modification of the Age-Related Eye Disease Study (AREDS) grading system and uses example slides from the Wisconsin Grading System (S2) and the International Classification System (S3) as guides. Affection status was defined by the most severe grade in either eye. All questionnaire data and samples were collected after informed consent was obtained.

Molecular Analyses

Genomic DNA was extracted from whole blood by the Duke CHG or Vanderbilt CHGR DNA banking cores using the PureGene system (Gentra Systems, Minneapolis, Minn.) on an Autopure LS. Genotyping was performed using Taqman on the ABI Prism 7900HT, and analyzed with the SDS software. SNP Assays-On-Demand or Assays-By-Design were obtained from Applied Biosystems Incorporated (Foster City, Calif.). The initial set of 44 SNPs was chosen to approximate a 500 Kb spacing between markers.

Exons of CFH were PCR amplified from genomic DNA, sequenced using Big Dye v3.1 (ABI) on an ABI 3730 automated sequencer, and analyzed using Mutation Surveyor software (Softgenetics, State College, Pa.). T1277C falls within a genomic duplication and could not be genotyped using Taq-Man assays. All individuals were sequenced using primers GGTTTCTTCTTGAAAATCACAGG (SEQ ID NO: 5) and CCATTGGTAAAACAAGGTGACA (SEQ ID NO: 6) to determine T1277C genotypes.

Statistical Analyses

Linkage disequilibrium and Hardy-Weinberg equilibrium calculations were done using Haploview version 3.0 using all case and control samples and one random individual from each of the families (S4). Haplotype blocks were defined using the D' parameter and the default definitions within Haploview. Allele frequency differences were tested using a $\chi^2$ test.

Single-locus and haplotype family-based association was tested using the Association in the Presence of Linkage (APL) method (S5) that performs a correct TDT-style test of association in the presence of linkage, using nuclear families with at least one affected individual and any number of unaffected siblings or parents. Odds ratios were calculated using standard logistic regression models (SAS version 9.1, SAS Institute, Cary, N.C.). The outcome variable was AMD affection status and genotypes were coded according to a log-additive model. Dose-response was tested using the $\chi^2$ test for trend.

Haplotype analysis in the case-control data set was tested using the "haplo.stats" program that uses a likelihood-based method to estimate haplotype frequencies (S6).

The 95% confidence interval for the population attributable risk percent (PAR %) for T1277C was calculated on the point estimate of the PAR % (43%), which was calculated from the combined frequency of genotypes CT and CC in controls and the unadjusted odds ratio (OR) of AMD for these genotypes relative to the TT reference group (S7). Calculation of the PAR % from case-control data assumes that the controls are representative of the general population and the disease is rare (<5% population prevalence across all exposure levels). PAR % calculated from OR adjusted for age and sex was similar.

We note that the P-value of the T1277C association in the family-based data set is not as significant as the P-value for the two original SNPs. This results from the ascertainment bias toward severe disease in the family collection, which results in an oversampling of T1277C-CC homozygotes. Family-based tests of association depend on both transmission and association. Oversampling for homozygosity reduces the power of any family-based transmission disequilibrium test. Since the original SNPs have low linkage disequilibrium values with T1277C ($r^2$=0.00 and 0.14 for rs2019724 and rd6428379, respectively), they were not oversampled for homozygosity to the extent of T1277C. In the case-control data set where the sampling bias is not as profound, the P-values for all three SNPs are similarly highly significant.

Haplotype Analysis

The five SNP haplotype block, defined by SNPs rs1831281, rs3753395, rs1853883, rs10494745, and rs6428279, identified five common haplotypes that capture over 95% of the haplotype variation (Table 2). The GAGGT haplotype is the most common in both the cases and controls, but is significantly more frequent in the cases.

TABLE 2

The haplotypes and their frequencies calculated from the case-control data. The haplotype consists of SNPs rs1831281, rs3753395, rs1853883, rs10494745, and rs6428279, respectively.

| Haplotype | Haplotype Frequency | |
| --- | --- | --- |
| | Cases | Controls |
| GAGGT | 0.46 | 0.33 |
| GAGAT | 0.16 | 0.11 |
| GACGC | 0.15 | 0.15 |
| ATCGC | 0.13 | 0.22 |
| GTCGC | 0.08 | 0.16 |
| Other | 0.02 | 0.03 |

TABLE 3

Location of SCR domains in protein.

| SCR | start aa position in mature protein | end aa position in mature protein | length | start in pre-protein | end in pre-protein |
| --- | --- | --- | --- | --- | --- |
| 1 | 1 | 62 | 62 | 19 | 80 |
| 2 | 63 | 123 | 61 | 81 | 141 |

TABLE 3-continued

Location of SCR domains in protein.

| SCR | start aa position in mature protein | end aa position in mature protein | length | start in pre-protein | end in pre-protein |
|---|---|---|---|---|---|
| 3 | 124 | 188 | 65 | 142 | 206 |
| 4 | 189 | 245 | 57 | 207 | 163 |
| 5 | 246 | 302 | 57 | 164 | 320 |
| 6 | 303 | 367 | 65 | 321 | 385 |
| 7 | 368 | 425 | 58 | 386 | 443 |
| 8 | 426 | 488 | 63 | 444 | 506 |
| 9 | 489 | 547 | 59 | 507 | 565 |
| 10 | 548 | 606 | 59 | 566 | 624 |
| 11 | 607 | 668 | 62 | 625 | 686 |
| 12 | 669 | 729 | 61 | 687 | 747 |
| 13 | 730 | 787 | 58 | 748 | 805 |
| 14 | 788 | 847 | 60 | 806 | 865 |
| 15 | 848 | 908 | 61 | 866 | 926 |
| 16 | 909 | 967 | 59 | 927 | 985 |
| 17 | 968 | 1026 | 59 | 986 | 1044 |
| 18 | 1027 | 1085 | 59 | 1045 | 1103 |
| 19 | 1086 | 1146 | 61 | 1104 | 1164 |
| 20 | 1147 | 1213 | 67 | 1165 | 1231 |

EXAMPLE 7

Linkage and Association Analysis

Resequencing of the LOC387715 and CUZD1 genes identified 21 known and 23 novel SNPs (Supplemental Tables 1 and 2). Sequencing primers and conditions are available from the authors (MAH) upon request. Of these 44 SNPs, 19 were genotyped in our entire dataset. Genotypes for all SNPs analyzed here were in Hardy-Weinberg equilibrium in unrelated controls (p>0.01). We observed high LD (D'>0.9) across a 60 kb region including a frequent coding SNP in exon 12 of PLEKHA1 (rs1045216), three coding SNPs in LOC387715 (rs10490923, rs2736911, rs10490924) and several additional non-coding PLEKHA1 and LOC387715 SNPs, replicating earlier observations (Rivera et al. 2005). Notably, the adjacent downstream gene PRSS11 (HtrA serine peptidase 1 (HTRA1), [MIM 602194]) was not included in this 60 kb region (FIG. 2).

In the family-based linkage analysis, a peak multipoint lod score was obtained at 124.7 Mb (HLOD 3.0 under affecteds-only dominant model, nonparametric LOD* 2.6, FIG. 1). SNP rs10664316 in LOC387715 (124.2 Mb) gave a maximum nonparametric two-point lod score of 3.2. In the case-control analysis, four highly correlated SNPs in the LOC387715 gene, including the frequent coding change rs10490924 in exon 1 previously implicated (Rivera et al. 2005), were very strongly associated with AMD, with logistic regression p-values on the order of $10^{-8}$ (table 5). The minor allele frequency (MAF) of these highly correlated SNPs was ~41.7% in cases, very similar to that reported by Rivera et al., and ~25.8% in controls, somewhat higher than the 19.6% reported by Rivera et al. Within the 60 kb LD block, and in the entire 122-127 Mb region, association signals of this order of magnitude were observed only for this set of highly correlated SNPs. In particular, the coding SNP in exon 12 of PLEKHA1 (rs1045216) showed substantially weaker evidence for association, both in terms of magnitude (odds ratio, OR) and statistical significance ($MAF_{cases}$: 28.2%, $MAF_{controls}$: 36.8%, OR=0.6, p=0.02). Unlike the previous reports, we detected a second region of association 400 kb distal to LOC387715 that included several SNPs in the CUZD1 gene and an even more distal SNP in the FAM24A gene (family with sequence similarity 24, member A [HGNC: 23470]). These SNPs, which were in LD with each other but not in LD with the associated SNPs in LOC387715 (FIG. 2), showed independent evidence for association with AMD risk, although at much lower statistical significance ($MAF_{cases}$: ~55%, $MAF_{controls}$: ~48%, p=0.0002-0.0058).

EXAMPLE 8

GIST Analysis

All SNPs with p-values ≦0.005 in the case-control analysis were analyzed with GIST to test if they explained the linkage signal in the region. Under the additive weighting scheme suggested by the case-control analysis (Li et al. 2004), only the four SNPs in the LOC387715 gene were significant in the GIST analysis (table 5). This suggests that the LOC387715 gene alone is responsible for the 10q26 linkage evidence.

EXAMPLE 9

Conditional Haplotype Analysis

With the combined case-control dataset, we used conditional haplotype modeling to identify the statistically most likely AMD susceptibility variant from among all the SNPs with strong evidence for association. We tested each SNP in table 5, conditioning on the risk allele of the most strongly associated SNP in CUZD1, FAM24A and LOC387715. Conditioning on the risk allele at rs1891110 in CUZD1, rs10490924 was strongly associated (p=7.6E-05) while none of the other SNPs were significant (p>0.05). Conditioning on the risk allele at rs2293435 in FAM24A, rs10490924 was strongly associated (p=7.1E-05) while none of the other SNPs were significant (p>0.05). Only conditioning on the risk allele at rs10490924 fully explained the association signal in the region, such that none of the other SNPs showed any evidence for association (p>0.6). Thus, this analysis also strongly implicates the LOC387715 gene alone in AMD, consistent with the Rivera et al. study.

EXAMPLE 10

Gene-Gene Interaction Analysis

We estimated joint odds ratios for all genotype combinations of the Y402H variant in CFH and the rs10490924 variant in LOC387715 (table 6). The TT/GG combination was used as the referent group. For individuals with the TT genotype at Y402H, the GT genotype at rs10490924 conferred a 2.7-fold increase in AMD risk (p=0.02) and the TT genotype conferred a 13.1-fold increase (p=0.003). For individuals with the CC genotype at Y402H, which conferred a 4-fold increase in AMD risk for TT genotypes at rs10490924 (p=0.0007), the GT genotype conferred a 12.6-fold increase in AMD risk (p<0.0001) and the TT genotype conferred a 23.8-fold increase (p<0.0001). Consistent with results of the AIC modeling strategy (table 7), the joint action of the Y402H and the rs10490924 variants was therefore best described by independent multiplicative effects, without statistically significant evidence for dominance effects or epistatic interaction. The joint effect of Y402H and rs10490924 accounted for 65.1% of the population attributable risk (PAR) of AMD (Bruzzi et al. 1985).

EXAMPLE 11

Case-Control Gene-Environment Interaction Analysis

Figure 3:
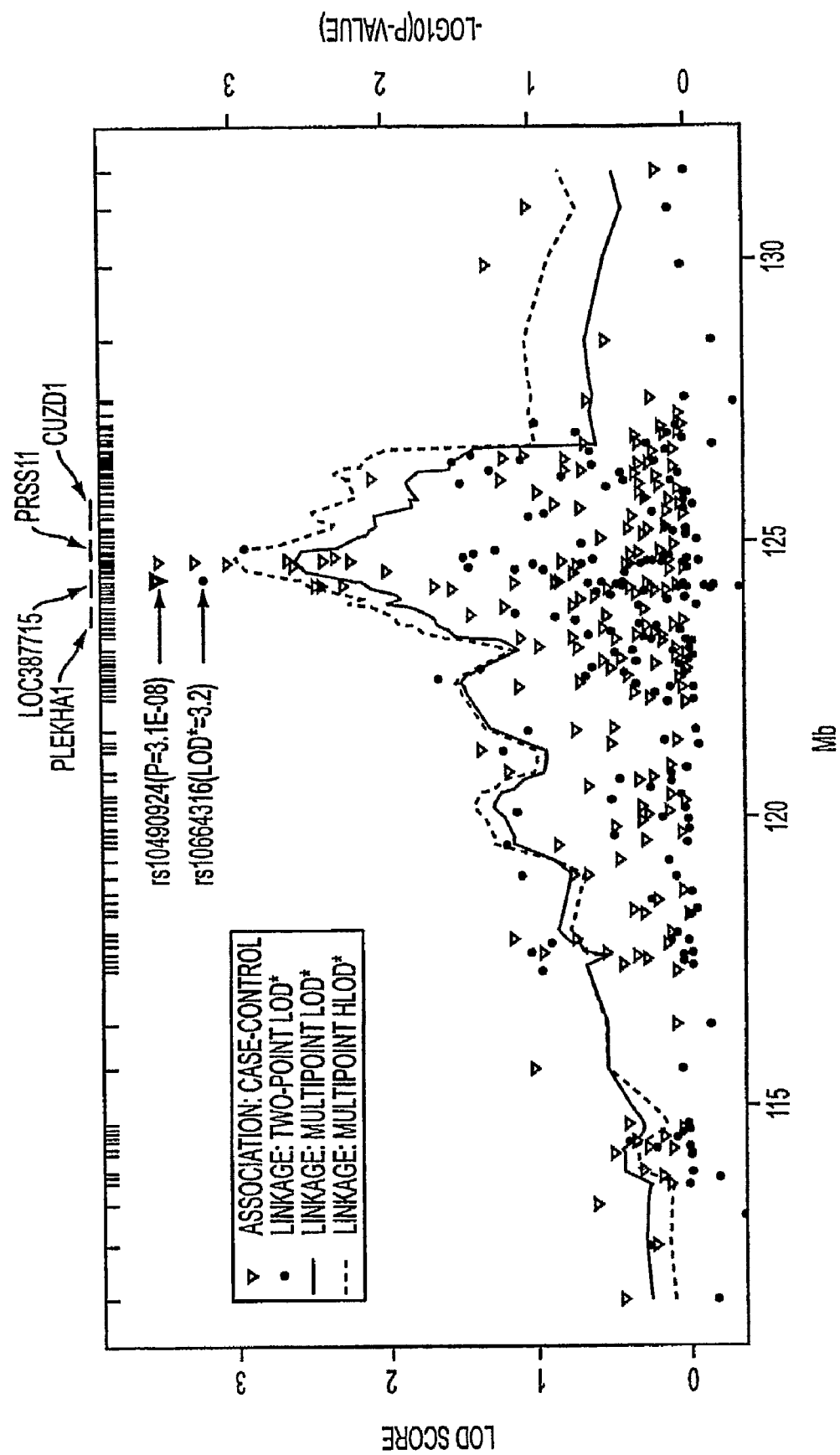
FIG. 3. Results of linkage (left axis: two-point and multipoint lod scores) and association analysis (right axis: $\log_{10}$-transformed p-values from logistic regression of case-control dataset, using additive coding described in text and adjusted for age and sex). For exact p-values in 122-127 Mb region that are smaller than $10^{-3}$, see Table 5.
Figure 5A:
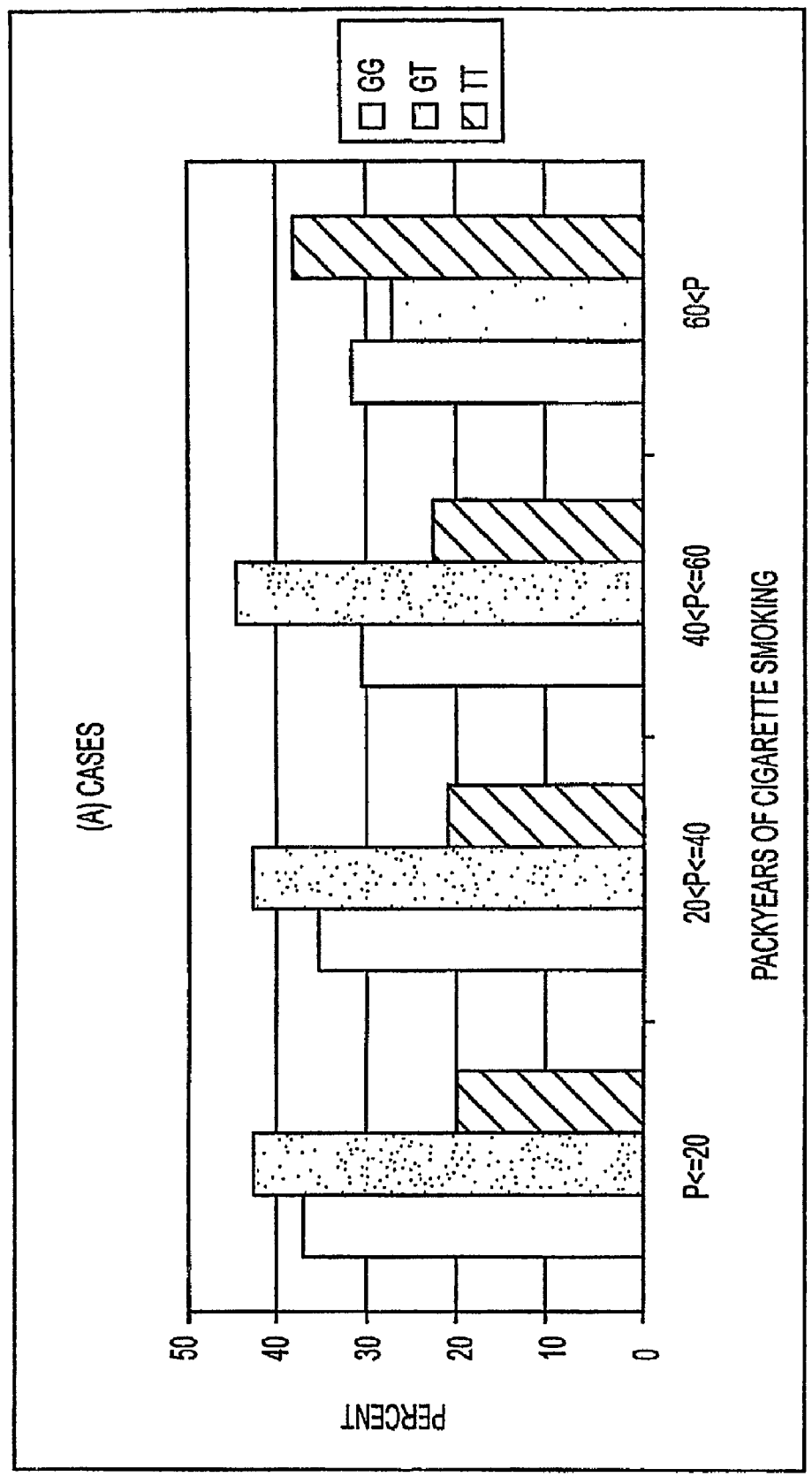
FIG. 5A. genotype frequencies at rs10490924 in unrelated AMD patients, by pack-years of cigarette smoking.
Figure 5B:
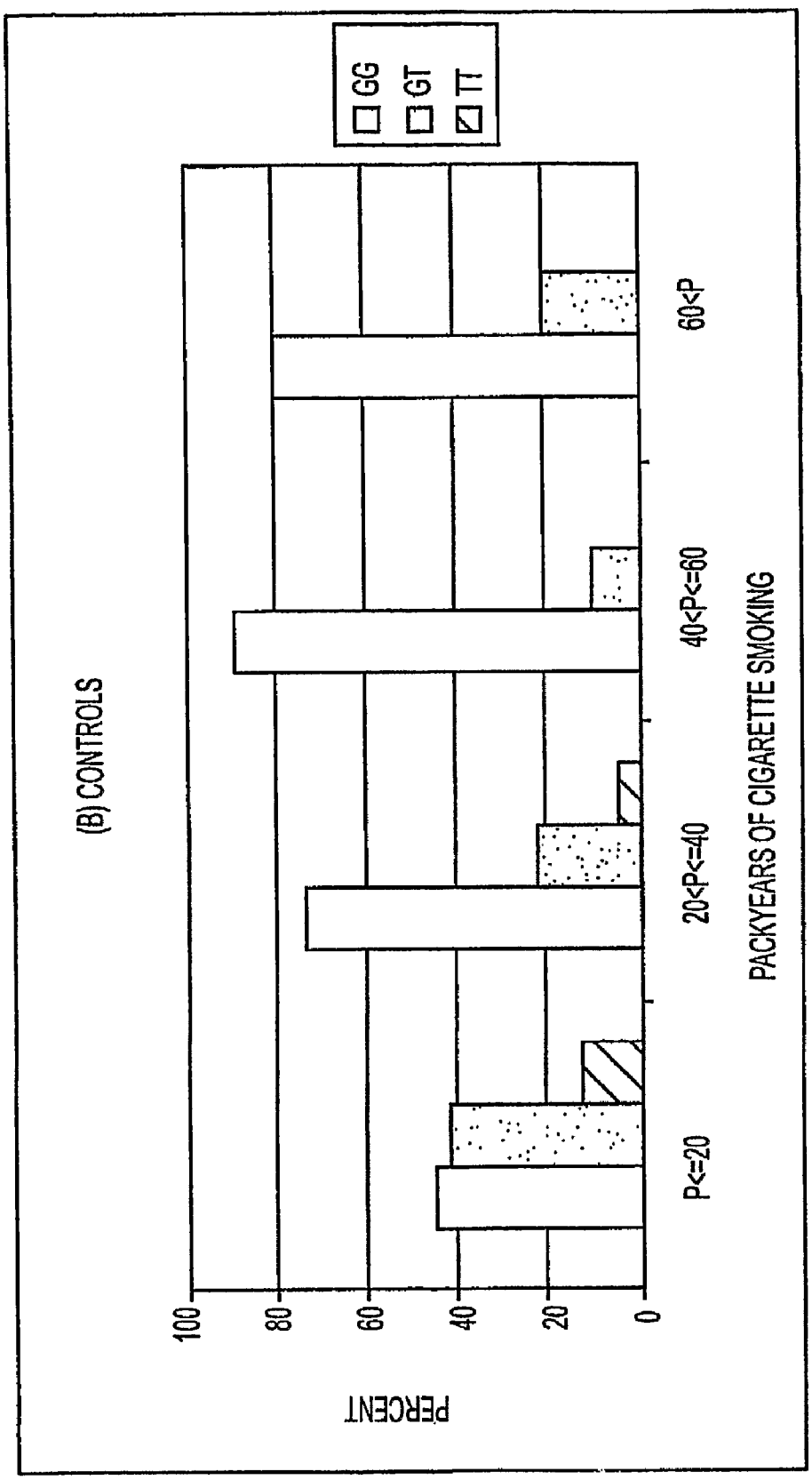
FIG. 5B, genotype frequencies at rs10490924 in unrelated controls without AMD, by pack-years of cigarette smoking FIG. 6. Ordered subset analysis of 90 multiplex AMD families with information on pack-years of cigarette smoking. Dashed line: Multipoint LOD* in 90 families. Solid line: Multipoint LOD* in 40 families with ≧44 pack-years, averaged across family members affected with AMD.
Figure 6:
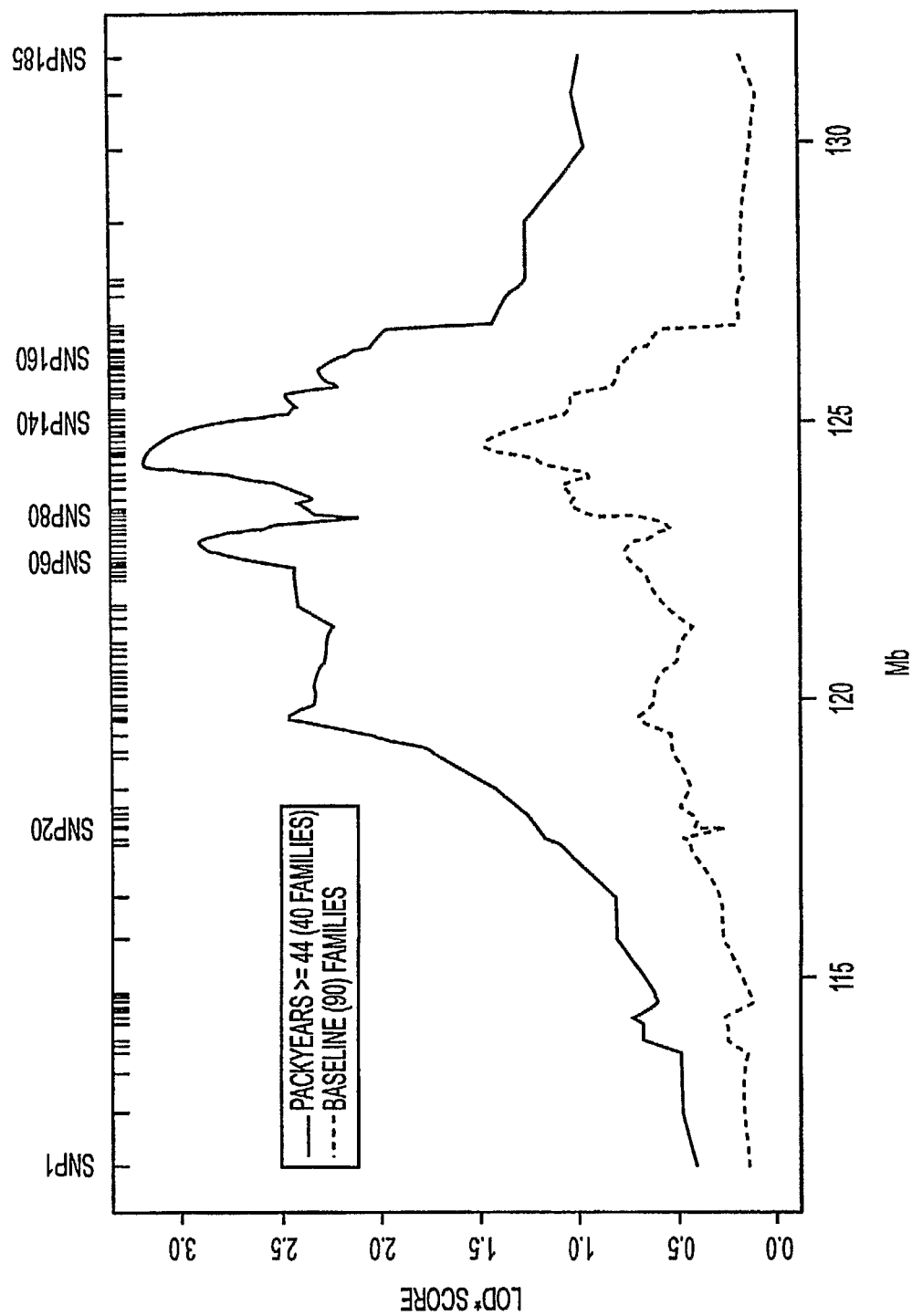

In contrast, we found strong evidence for statistical interaction of smoking and genotypes at rs10490924. The model with the ADD_SMOKE_INT term provided a significantly better fit to the data by 5.2 AIC units, compared to the model without this term (table 7). A significant product term with positive regression coefficient for smoking and rs10490924 in the logistic regression model indicated more than multiplicative joint effects (p=0.007). In our dataset, the presence of the LOC387715 susceptibility allele did not confer a significantly increased risk of AMD to non-smokers (p=0.59 for GT genotype, p=0.12 for TT genotype, table 8), while the GT genotype in smokers increased the risk 2.7-fold (p=0.001) and the TT genotype in smokers increased the risk 8.2-fold (p<0.0001). A case-only analysis of rs10490924 and pack-years of smoking (as a continuous variable) also supported the presence of gene-environment interaction (p=0.05 adjusted for age and sex). The relative frequency of TT genotypes in affected individuals increased almost linearly with increasing pack-years of smoking, with a corresponding decrease of GG genotype frequencies (FIG. 3, panel A). This pattern was strikingly similar to results for simulated data when the disease status was generated with a logistic regression model including a gene-environment interaction term (Schmidt et al. 2005). Genotype frequencies at rs10490924 were not related to pack-years of smoking in our control sample (FIG. 5B), confirming that the result in cases was due to gene-environment interaction rather than population correlation of the two factors. The joint effect of rs10490924 and smoking accounted for 34.3% of the PAR of AMD.

EXAMPLE 12

Family-Based Gene-Environment Interaction Analysis

Figure 4:
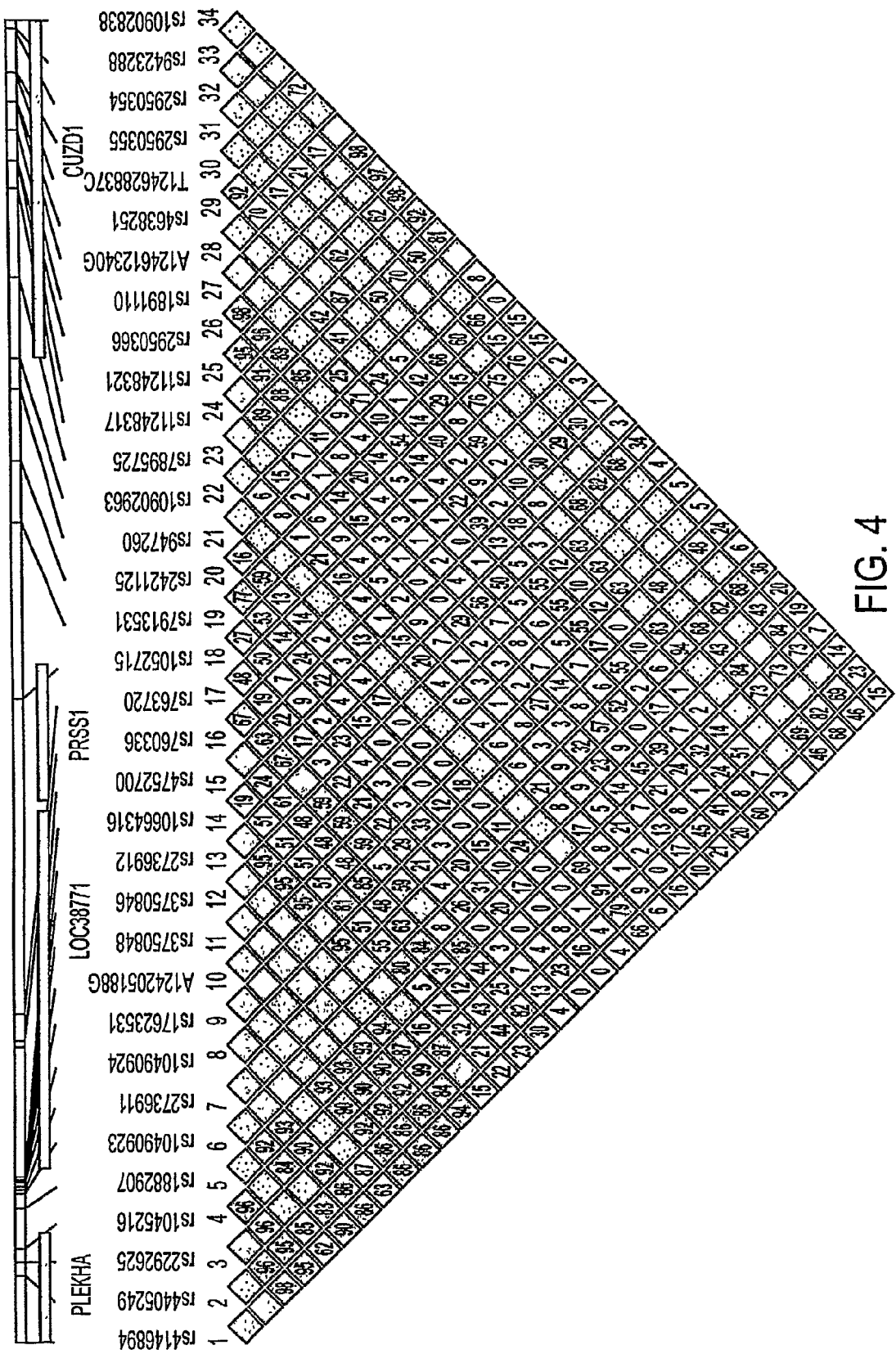
FIG. 4. LD pattern in region from PLEKHA1 [MIM 607772] to CUZD1 [HGNC 17937]. The relative physical position of each SNP is given in the upper diagram, and the pairwise D' between all SNPs is given below each SNP combination. Red-shaded squares indicate D' values >0.80. D'=1.0 when no number is given, which is either significant (dark-red shading) or non-significant (blue shading) based on the Haploview default definition (Gabriel et al. 2002)

The highly significant association of AMD with rs10490924 that was observed in the initial case-control analysis was not replicated in the family-based analysis with APL. This could be due to the smaller size of our family-based dataset, or to between-family heterogeneity. To test the latter possibility, we applied OSA to our multiplex family dataset, using the average pack-years of smoking in affected individuals as the OSA covariate (ordered from high to low). OSA indicated that the majority of linkage evidence in the 10q26 region was contributed by only 40 families with an average of 44 pack-years of smoking (FIG. 4). The difference in nonparametric lod scores between the 90 multiplex families with sufficient information to calculate average smoking pack-years and the 40 families with heavy smokers was significant (p=0.048), based on 10,000 runs of the OSA permutation test (Hauser et al. 2004). When the APL analysis was repeated using only multiplex and singleton families which met the "heavy smoking" criterion in affected individuals (family-average of 44 pack-years of smoking, 46 families total), the results confirmed the case-control association analysis: The APL p-value for rs10490924 and rs3750848 in LOC387715 was 0.02. Three SNPs in other genes also had p-values of 0.02: rs760336 in PRSS11 adjacent to LOC387715, rs1052715 in DMBT1 (deleted in malignant brain tumors 1 [MIM 601969]) and hcv2917031 in GPR26 (G protein-coupled receptor 26 [MIM 604847]). Neither SNP had a case-control association p-value<0.05 in the overall analysis.

EXAMPLE 13

Clinical Subgroup Analysis

It is of great clinical interest to determine whether the modification of the LOC387715 association by cigarette smoking is observed in both geographic atrophy (GA, grade 4) and neovascular AMD (CNV, grade 5). Table 9 shows that the strong association with LOC387715 in smokers was primarily due to genotype frequency differences between grade 1 controls (8.3% with genotype TT) and CNV patients (29.3% with genotype TT). When all genotyped individuals regardless of smoking history information were evaluated, the frequency of the T allele was higher in patients with CNV (47.6%) compared to GA (39.0%). Our dataset had limited statistical power for the AMD subtype comparison since it included a much smaller number of GA patients, compared to CNV patients (table 4), and since smoking history information was not available for all study participants.

EXAMPLE 14

Relates to Examples 7-13

Study Population

As part of an ongoing large-scale study of genetic and environmental risk factors for AMD, we have ascertained AMD patients, their affected and unaffected family members, and a group of unrelated controls of similar age and ethnic background at two sites in the Southeastern United States: Duke University Eye Center (DUEC) and Vanderbilt University Medical Center (VUMC). Using stereoscopic color fundus photographs, all enrolled individuals were assigned (by EAP and AA) one of five different grades of macular findings, as described previously (Schmidt et al. 2000; Seddon et al. 1997) and summarized in Table 4. Our AMD classification is a modification of the AREDS grading system, using Wisconsin grading system example slides (Klein et al. 1991) and the International Classification System (Bird et al. 1995) as guides. The more severely affected eye was used to classify individuals. Unrelated controls were enrolled via (i) study advertisement in DUEC- and VUMC-affiliated newsletters; (ii) recruitment presentations by study coordinators at local retirement communities, which were likely to obtain health care at DUEC or VUMC, respectively; and (iii) AMD-related seminars for the general public sponsored by DUEC or VUMC opthalmology clinics. Spouses of AMD patients were also asked to participate as controls. All cases and controls included in this study were white and at least 55 years of age. The study protocol was approved by the Institutional Review Boards (IRB) of the Duke University Medical Center and VUMC, the research adhered to the tenets of the Declaration of Helsinki, and informed consent was obtained from all study participants. Blood samples were collected and genomic DNA was extracted from whole blood using the PureGene system (Gentra Systems, Minneapolis, Minn.) on an Autopure LS.

Information about the smoking history of study participants was obtained from a self-administered questionnaire that was formatted to maximize readability for individuals with low vision. However, if participants indicated that they could not complete the form, a project coordinator offered to assist the participants in filling out the questionnaire. Regular cigarette smoking was assessed by two questions: 1) "Have you smoked at least 100 cigarettes in your lifetime?" and 2) "Did you ever smoke cigarettes at least once per week?" Individuals answering "yes" to both questions were asked the average number of cigarettes they smoked per day, the year that they started smoking, whether they had quit smoking, and if so, what year. This information was used to calculate pack-years of smoking as (cigarettes per day*years smoked)/20 cigarettes per pack. The most general measurement of smoking history was constructed as an "ever/never" variable based on a participant's response to question 1) above.

The study population for the analysis presented here included 810 unrelated AMD patients with early (grade 3) or advanced (grades 4 and 5) AMD. Of these, 200 had at least one sampled (affected or unaffected) relative and thus contributed to the family-based association analysis. The remaining 610 AMD patients without sampled relatives, and 259 unrelated controls without AMD (grades 1 and 2), made up an independent case-control dataset. Demographic and clinical information for these individuals is shown in table 4.

Genotyping, Linkage and Association Analysis

Previous work by our group (Kenealy et al. 2004) and others (Weeks et al. 2004; Majewski et al. 2003; Seddon et al. 2003; Iyengar et al. 2004) suggested the presence of an AMD susceptibility locus on chromosome 10q26, with the linkage peak centered at approximately 122 Mb. To narrow down the region most likely to harbor an AMD susceptibility allele, we genotyped 103 SNPs in the 112 to 132 Mb interval, extending 10 Mb to either side of the reported linkage peak. We started with a density of approximately 1 SNP per 1 Mb and filled in the 117-127 Mb region immediately surrounding the 122 Mb peak with a higher density of one SNP per 140 kb on average. All SNPs were selected using SNPSelector software (Xu et al. 2005) to have approximately equal spacing with minor allele frequency $\geq 5\%$. Genotyping was performed with the TaqMan allelic discrimination assay, using either Assays-On-Demand or Assays-By-Design products from Applied Biosystems. For quality control (QC) procedures, two CEPH standards were included on each 96-well plate, and samples from six individuals were duplicated across all plates, with the laboratory technicians blinded to their identities. Analysis required matching QC genotypes within and across plates and at least 95% genotyping efficiency. The Y402H variant of the CFH gene was genotyped by sequencing, as previously described (Haines et al. 2005).

Following the first round of genotyping and statistical analysis, we applied iterative association mapping (Oliveira et al. 2005) to select another set of SNPs in the peak region, defined approximately as the 1-lod-score-unit support interval surrounding the peak multipoint lod score. In addition to using SNPSelector (Xu et al. 2005), SNPs were identified through resequencing of the LOC387715 gene and the CUZD1 gene (CUB and zona pellucida-like domains 1 [HGNC: 17937]) in 48-72 unrelated affected and unaffected individuals. Our final SNP density was an average of one SNP per 43 kb, for a total of 117 SNPs in the 122-127 Mb region, and an average of one SNP every 220 kb outside of this interval, for a total of 185 SNPs in the 112-132 Mb region.

The genotype data were analyzed with MERLIN (Abecasis et al. 2002) to calculate nonparametric two-point and multipoint LOD* scores (Kong and Cox 1997), using the exponential model. Allele frequencies were estimated from all genotyped individuals. Parametric affecteds-only heterogeneity lod scores (HLODs) assuming a dominant (disease allele frequency 0.01) or recessive (disease allele frequency 0.2) model were also computed with MERLIN. To avoid an inflation of linkage evidence due to inter-marker linkage disequilibrium (LD) (Boyles et al. 2005), we used recently described methods based on estimated haplotype frequencies of SNP clusters in high pairwise LD, using a threshold of $r^2$=0.16 to define these clusters (Abecasis and Wigginton 2005). The LD pattern in the region of interest was analyzed with the Haploview program (Barrett et al. 2005), using the generated genotypes from unrelated AMD patients as the input. Association analysis was applied to all SNPs in the 122-127 Mb region, using the family-based Association in the Presence of Linkage (APL) test (Martin et al. 2003) and standard logistic regression analysis for case-control comparisons with adjustment for age and sex (SAS version 8.02, SAS Institute Inc., Cary, N.C.). An additive coding scheme was used, with the SNP model covariate taking on values −1, 0 and 1 for genotypes 1/1, 1/2, and 2/2, and 2 being the minor allele in controls. As described above, we divided our total sample into cases contributing to the APL analysis (affected individuals with at least one sampled relative, n=200 families), and an independent sample of cases without sampled relatives (n=610) who were compared to 259 unrelated controls. We used the Genotype-IBD Sharing Test (GIST) method (Li et al. 2004) to examine which of the most strongly associated SNPs best explained the linkage evidence in the region. We also used the COCAPHASE module of the UNPHASED software package (Dudbridge 2003) to perform conditional haplotype analysis. This analysis tested whether conditioning on the risk allele at a particular SNP accounted for the association signal in the region. If the association signal in the region was driven by a single SNP, conditioning on its effect was expected to remove all evidence of association for the remaining SNPs.

Interaction Analysis

We conducted additional analyses to incorporate effects of the two most important known AMD risk factors, smoking and the CFH gene. First, we fit a series of logistic regression models to the combined case-control data set (including probands from family-based dataset) to identify the model that best described (1) the joint effects of CFH and LOC387715, and (2) the joint effects of smoking and LOC387715. We followed a recently proposed modeling strategy (North et al. 2005) in which the best-fitting model was derived on the basis of Akaike's Information Criterion (AIC). The AIC compares different models with a log-likelihood ratio test that is penalized for the number of model parameters to identify the most parsimonious model that adequately fits the data. For each genotype, two model terms were tested: one coding for additive effects at the first, second, or both loci (ADD1, ADD2, ADDBOTH), using the coding described above, and the other one coding for dominance effects (DOM1, DOM2, DOMBOTH), with a value of −0.5 for genotypes 1/1 and 2/2, and a value of 0.5 for genotype 1/2. Three additional models (ADDINT, ADDDOM, DOMINT) were fit to test for deviation from joint additive or joint dominance effects of CFH and LOC387715, and two additional models (ADD_SMOKE_INT, DOM_SMOKE_INT) were fit for LOC387715 and smoking (comparing ever- vs. never-smokers). Models for which the AIC differed by less than 2 units were considered statistically indistinguishable (North et al. 2005), and the model with fewer parameters was chosen as the best fitting one. For example, when the addition of the ADDINT term did not provide a substantially better model fit, this was interpreted as lack of evidence for statistical interaction between the two factors. Thus, they each had independent main effects that were multiplicative (additive on the logarithmic scale) such that the best estimate of the odds ratio for being exposed to both factors was the product of the two main effect odds ratios.

Our second approach for incorporating AMD-associated covariates was motivated by earlier reports of the 10q26 linkage evidence being due primarily to families with heavy smokers (Weeks et al. 2004). Similar to the previous study, we used an ordered subset analysis (OSA) (Hauser et al. 2004) with the family-average of smoking pack-years as a covariate.

To avoid an undue influence of zero pack-years values on family averages, pack-years were coded as missing for non-smokers. Using the high-to-low ordering of family-averaged pack-years, OSA tested whether a subset of families with heavy smokers provided significantly greater linkage evidence than the reference dataset, which in this case was restricted to families for whom non-missing covariate values could be computed. Thus, the baseline lod score was computed for families in which there was at least one affected smoker with pack-years information.

REFERENCES

The disclosure of each reference cited is expressly incorporated herein for the purpose to which is referenced in the text.
1. Centers for Disease Control and Prevention (CDC), *MMWR Morb. Mortal. Wkly. Rep.* 53, 1069 (2004).
2. J. Ambati, B. K. Ambati, S. H. Yoo, S. Ianchulev, A. P. Adamis, *Surv. Opthalmol.* 48, 257 (2003).
3. C. C. Klayer et al., *Arch. Opthalmol.* 116, 1646 (1998).
4. C. J. Hammond et al., *Opthalmology.* 109, 730 (2002).
5. M. Heiba, R. C. Elston, B. E. Klein, R. Klein, *Genet. Epidemiol.* 11, 51 (1994).
6. E. M. Stone et al., *Nat. Genet.* 20, 328 (1998).
7. S. Schmidt et al., *Ophthalmic Genet.* 23, 209 (2002).
8. E. M. Stone et al., *N. Engl. J. Med.* 351, 346 (2004).
9. D. E. Weeks et al., *Am. J. Hum. Genet.* 75, 174 (2004).
10. G. R. Abecasis et al., *Am. J. Hum. Genet.* 74, 482 (2004).
11. S. K. Iyengar et al., *Am. J. Hum. Genet.* 74, 20 (2004).
12. Materials and methods are provided in Examples 6.
13. D. C. Rodriguez, J. Esparza-Gordillo, d. J. Goicoechea, M. Lopez-Trascasa, P. Sanchez-Conal, *Mol. Immunol.* 41, 355 (2004).
14. J. M. Seddon, G. Gensler, R. C. Milton, M. L. Klein, N. Rifai, *JAMA* 291, 704 (2004).
15. D. H. Gurne, M. O. Tso, D. P. Edward, H. Ripps, *Opthalmology.* 98, 602 (1991).
16. M. C. Killingsworth, J. P. Sarks, S. H. Sarks, *Eye* 4 (Pt 4), 613 (1990).
17. R. F. Mullins, S. R. Russell, D. H. Anderson, G. S. Hageman, *FASEB J.* 14, 835 (2000).
18. T. K. Blackmore, V. A. Fischetti, T. A. Sadlon, H. M. Ward, D. L. Gordon, *Infect. Immun.* 66, 1427 (1998).
19. E. Giannakis et al., *Eur. J. Immunol.* 33, 962 (2003).
20. D. T. Fearon, *Proc. Natl. Acad. Sci. U.S.A* 75, 1971 (1978).
21. C. Mold, M. Kingzette, H. Gewurz, *J. Immunol.* 133, 882 (1984).
22. R. Oksjoki et al., *Arterioscler. Thromb. Vasc. Biol.* 23, 630 (2003).
23. J. Esparza-Gordillo et al., *Immunogenetics* 56, 77 (2004).
S1. J. M. Seddon, U. A. Ajani, B. D. Mitchell, *Am. J. Opthalmol.* 123, 199 (1997).
S2. The Age-Related Eye Disease Study Research Group, *Control Clin. Trials* 20, 573 (1999).
S3. C. Bird et al., *Survey of Opthalmology* 39, 367 (1995).
S4. J. C. Barrett, B. Fry, J. Maller, M. J. Daly, *Bioinformatics.* 21, 263 (2005).
S5. E. R. Martin, M. P. Bass, E. R. Hauser, N. L. Kaplan, *Am. J. Hum. Genet.* 73, 1016 (2003).
S6. S. L. Lake et al., *Hum. Hered.* 55, 56 (2003).
S7. N. E. Breslow, N. E. Day, *IARC Sci. Publ.* 32, 5 (1980).

ADDITIONAL REFERENCES

Abecasis G R, Cherny S S, Cookson W O, and Cardon L R (2002) Merlin-rapid analysis of dense genetic maps using sparse gene flow trees. Nat Genet. 30:97-101

Abecasis G R and Wigginton J E (2005) Handling marker-marker linkage disequilibrium: pedigree analysis with clustered markers. Am J Hum Genet. 77:754-767

Boyles A L, Scott W K, Martin E R, Schmidt S, Li Y J, Ashley-Koch A, Bass M P, Schmidt M, Pericak-Vance M A, Speer M C, and Hauser E R (2005) Linkage disequilibrium inflates type I error rates in multipoint linkage analysis when parental genotypes are missing. Hum Hered 59:220-227

Bruzzi P, Green S B, Byar D P, Brinton L A, and Schairer C (1985) Estimating the population attributable risk for multiple risk factors using case-control data. Am J Epidemiol 122:904-914

Conley Y P, Thalamuthu A, Jakobsdottir J, Weeks D E, Mali T, Ferrell R E, and Gorin M B (2005) Candidate gene analysis suggests a role for fatty acid biosynthesis and regulation of the complement system in the etiology of age-related maculopathy. Hum Mol Genet 14:1991-2002

Dudbridge F (2003) Pedigree disequilibrium tests for multilocus haplotypes. Genet Epidemiol 25:115-121

Edwards A O, Ritter R, III, Abel K J, Manning A, Panhuysen C, and Farrer L A (2005) Complement factor H polymorphism and age-related macular degeneration. Science 308: 421-424

Fisher S A, Abecasis G R, Yashar B M, Zareparsi S, Swaroop A, Iyengar S K, Klein B E, Klein R, Lee K E, Majewski J, Schultz D W, Klein M L, Seddon J M, Santangelo S L, Weeks D E, Conley Y P, Mah T S, Schmidt S, Haines J L, Pericak-Vance M A, Gorin M B, Schulz H L, Pardi F, Lewis C M, and Weber B H (2005) Meta-analysis of genome scans of age-related macular degeneration. Hum Mol Genet 14:2257-2264

Gabriel S B, Schaffner S F, Nguyen H, Moore J M, Roy J, Blumenstiel B, Higgins J, DeFelice M, Lochner A, Faggart M, Liu-Cordero S N, Rotimi C, Adeyemo A, Cooper R, Ward R, Lander E S, Daly M J, and Altshuler D (2002) The structure of haplotype blocks in the human genome. Science 296:2225-2229

Hageman G S, Anderson D H, Johnson L V, Hancox L S, Taiber A J, Hardisty L I, Hageman J L et al (2005) A common haplotype in the complement regulatory gene factor H (HF1/CFH) predisposes individuals to age-related macular degeneration. Proc Natl Acad Sci USA Haines J L, Hauser M A, Schmidt S, Scott W K, Olson L M, Gallins P, Spencer K L, Kwan S Y, Noureddine M, Gilbert J R, Schnetz-Boutaud N, Agarwal A, Postel E A, and Pericak-Vance M A (2005) Complement factor H variant increases the risk of age-related macular degeneration. Science 308:419-421

Hauser E R, Watanabe R M, Duren W L, Bass M P, Langefeld C D, and Boehnke M (2004) Ordered subset analysis in genetic linkage mapping of complex traits. Genet Epidemiol 27:53-63

Ioamidis J P, Ntzani E E, Trikalinos T A, and Contopoulos-Ioannidis D G (2001) Replication validity of genetic association studies. Nat Genet 29:306-309

Jakobsdottir J, Conley Y P, Weeks D E, Mah T S, Ferrell R E, and Gorin M B (2005) Susceptibility genes for age-related maculopathy on chromosome 10q26. Am J Hum Genet 77:389-407

Kenealy S J, Schmidt S, Agarwal A, Postel E A, De La Paz M A, Pericak-Vance M A, and Haines J L (2004) Linkage analysis for age-related macular degeneration supports a gene on chromosome 10q26. Mol Vis 10:57-61

Klayer C C W, Assink J J M, van Leeuwen R, Wolfs R C W, Vingerling J R, Stijnen T, Hofman A, and De Jong P T V M (2001) Incidence and progression rates of age-related maculopathy: The Rotterdam study. Invest Opthalmol Vis Sci 42:2237-2241

Klein R, Davis M D, Magli Y L, Segal P, Klein B E, and Hubbard L (1991) The Wisconsin age-related maculopathy grading system. Opthalmology 98:1128-1134

Klein R, Klein B E, Tomany S C, and Cruickshanks K J (2003) The association of cardiovascular disease with the long-term incidence of age-related maculopathy: the Beaver Dam Eye Study. Opthalmology 110:1273-1280

Klein R, Peto T, Bird A, and Vannewkirk M R (2004) The epidemiology of age-related macular degeneration. Am J Opthalmol 137:486-495

Klein R J, Zeiss C, Chew E Y, Tsai J Y, Sadder R S, Haynes C, Henning A K, Sangiovanni J P, Mane S M, Mayne S T, Bracken M B, Ferris F L, Ott J, Barnstable C, and Hoh J (2005) Complement factor H polymorphism in age-related macular degeneration. Science 308:385-389

Kong A and Cox N J (1997) Allele-sharing models: LOD scores and accurate linkage tests. Am J Hum Genet 61:1179-1188

Li C, Scott L J, and Boehnke M (2004) Assessing Whether an Allele Can Account in Part for a Linkage Signal: The Genotype-IBD Sharing Test (GIST). Am J Hum Genet 74:418-431

Lohmueller K E, Pearce C L, Pike M, Lander E S, and Hirschhorn J N (2003) Meta-analysis of genetic association studies supports a contribution of common variants to susceptibility to common disease. Nat Genet 33:177-182

Majewski J, Schultz D W, Weleber R G, Schain M B, Edwards A O, Matise T C, Acott T S, Ott J, and Klein M L (2003) Age-related macular degeneration—a genome scan in extended families. Am J Hum Genet 73:540-550

North B V, Curtis D, and Sham P C (2005) Application of logistic regression to case-control association studies involving two causative loci. Hum Hered 59:79-87

Oliveira S A, Li Y J, Noureddine M A, Zuchner S, Qin X, Pericak-Vance M A, and Vance J M (2005) Identification of Risk and Age-at-Onset Genes on Chromosome 1 p in Parkinson Disease. Am J Hum Genet 77:252-264

Rivera A, Fisher S A, Fritsche L G, Keilhauer C N, Lichtner P, Meitinger T, and Weber B H (2005) Hypothetical LOC387715 is a second major susceptibility gene for age-related macular degeneration, contributing independently of complement factor H to disease risk. Hum Mol Genet 14:3227-3236

Schmidt M, Hauser E R, Martin E R, and Schmidt S (2005) Extension of the SIMLA package for generating pedigrees with complex inheritance patterns: Environmental covariates, gene-gene and gene-environment interaction. Stat Appl Genet Mol Biol 4:1

Schmidt S, Saunders A M, De La Paz M A, Postel E A, Heinis R M, Agarwal A, Scott W K, Gilbert J R, McDowell J G, Bazyk A, Gass J D, Haines J L, and Pericak-Vance M A (2000) Association of the apolipoprotein E gene with age-related macular degeneration: possible effect modification by family history, age, and gender. Mol Vis 6:287-293

Scott W K, Schmidt S, Hauser M A, Gallins P, Kwan S, Olson L M, Schnetz-Boutaud N, Spencer K L, Gilbert J R, Agarwal A, Postel E A, Haines J L, and Pericak-Vance M A (2005) Interaction of CFH T1277C polymorphism and cigarette smoking in age-related macular degeneration. American Society of Human Genetics 55th Annual Meeting, Salt Lake City, Utah Seddon J M, Santangelo S L, Book K, Chong S, and Cote J (2003) A genomewide scan for age-related macular degeneration provides evidence for linkage to several chromosomal regions. Am J Hum Genet 73:780-790

Smith W, Assink J, Klein R, Mitchell P, Klayer C C, Klein B E, Hofman A, Jensen S, Wang J J, and de Jong P T (2001) Risk factors for age-related macular degeneration: Pooled findings from three continents. Opthalmology 108:697-704 van Leeuwen R, Klayer C C, Vingerling J R, Hofman A, and de Jong P T (2003) The risk and natural course of age-related maculopathy: follow-up at 6½years in the Rotterdam study. Arch Opthalmol 121:519-526

Xu H, Gregory S G, Hauser E R, Stenger J E, Pericak-Vance M A, Vance J M, Zuchner S, and Hauser M A (2005) SNPselector: a web tool for selecting SNPs for genetic association studies. BioInformatics 21:4181-4186

Zareparsi S, Branham K E, Li M, Shah S, Klein R J, Ott J, Hoh J, Abecasis G R, and Swaroop A (2005) Strong Association of the Y402H Variant in Complement Factor H at 1q32 with Susceptibility to Age-Related Macular Degeneration. Am J Hum Genet 77:149-153

Web Resources

Online Mendelian Inheritance in Man (OMIM),. HUGO Gene Nomenclature Committee (HGNC) Software for Ordered Subset Analysis and Association in the Presence of Linkage Test, Software for Genotype-IBD Sharing Test, and UNPHASED software.

We claim:

1. A method to assess risk of AMD in a patient comprising:
   determining whether the patient has a T allele at rs10490924;
   determining whether the patient is a cigarette smoker; and
   identifying the patient as:
   being at high risk of AMD if the patient has the T allele and is a cigarette smoker,
   being at lower risk of AMD if the patient has the T allele but is not a cigarette smoker or is a cigarette smoker but does not have the T allele, and
   being at lowest risk if the patient does not have the T allele and is not a cigarette smoker.

2. A method to assess risk of and treat AMD in a patient comprising:
   determining whether the patient has a T allele at rs10490924;
   determining whether the patient is a cigarette smoker; and
   providing the patient with a behavioral therapy to encourage smoking cessation if the patient has the T allele at rs10490924 and is a cigarette smoker.

3. A method to assess risk of and treat AMD in a patient comprising:
   determining whether the patient has a T allele at rs10490924;
   determining whether the patient is a cigarette smoker; and
   providing the patient with smokeless nicotine to encourage smoking cessation if the patient as the T allele and is a cigarette smoker.

4. The method of claim 2 wherein the step of providing comprises prescribing the behavioral therapy.

5. The method of claim 2 wherein the behavioral therapy is counseling.

6. The method of claim 2 wherein the behavioral therapy is a class.

7. The method of claim 2 wherein the behavioral therapy is information.

8. The method of claim 2 wherein the information is printed matter.

9. The method of claim 2 wherein the information is on a data storage medium.

10. The method of claim 2 wherein the information is on an audio tape.

11. The method of claim 2 wherein the information is on a video tape.

12. The method of claim 3 wherein the smokeless nicotine is nicotine gum.

13. The method of claim 3 wherein the smokeless nicotine is in a transdermal patch.

14. The method of claim 3 wherein the smokeless nicotine is in a nasal spray.

15. The method of claim 3 wherein the smokeless nicotine is in an inhaler.

16. The method of claim 3 wherein the step of providing comprises prescribing or recommending a form of smokeless nicotine.

17. The method of claim 1 further comprising determining if the patient has a variant of Complement Factor H protein or coding sequence.

18. The method of claim 17 wherein a variant protein is determined.

19. The method of claim 17 wherein a variant coding sequence is determined.

* * * * *